(12) United States Patent
Nguyen et al.

(10) Patent No.: US 8,105,610 B2
(45) Date of Patent: Jan. 31, 2012

(54) METHOD OF MAKING NOVEL ERYTHROVIRUS V9 VP2 CAPSID POLYPEPTIDES

(75) Inventors: Quang Tri Nguyen, Ivry sur Seine (FR); Antoine Garbarg-Chenon, Paris (FR); Véronique Auguste, Paris (FR)

(73) Assignee: Assistance Publique Hospitaux de Paris, Paris (FR)

( * ) Notice: Subject to any disclaimer, the term of this patent is extended or adjusted under 35 U.S.C. 154(b) by 739 days.

(21) Appl. No.: 11/868,380

(22) Filed: Oct. 5, 2007

(65) Prior Publication Data

US 2008/0248528 A1 Oct. 9, 2008

Related U.S. Application Data

(62) Division of application No. 09/555,640, filed on Aug. 10, 2000, now Pat. No. 7,291,452.

(30) Foreign Application Priority Data

Dec. 3, 1997 (FR) ..................................... 97 15197

(51) Int. Cl.
*A61K 39/23* (2006.01)
*C12P 21/06* (2006.01)
(52) U.S. Cl. ..................................... 424/233.1; 435/69.1
(58) Field of Classification Search .......................... None
See application file for complete search history.

(56) References Cited

U.S. PATENT DOCUMENTS

| | | | |
|---|---|---|---|
| 5,508,186 A | 4/1996 | Young et al. | |
| 5,827,647 A | 10/1998 | Young et al. | |
| 5,905,040 A | 5/1999 | Mazzara et al. | |
| 6,132,732 A | 10/2000 | Young et al. | |
| 6,204,044 B1 | 3/2001 | Brown | |
| 6,274,307 B1 * | 8/2001 | Soutschek et al. | 435/5 |
| 6,287,815 B1 * | 9/2001 | Brown | 435/69.3 |
| 6,379,885 B1 | 4/2002 | Brown | |
| 7,291,452 B1 | 11/2007 | Nguyen et al. | |

FOREIGN PATENT DOCUMENTS

| | | |
|---|---|---|
| DE | 40 03 826 A1 | 8/1991 |
| EP | 0514413 | 2/1991 |
| EP | 1037916 | 12/1998 |
| EP | 0491824 | 4/2006 |
| JP | 7-147986 | 10/1997 |
| WO | WO 91/12269 | 8/1991 |
| WO | WO 96/09391 | 3/1996 |
| WO | WO-01/06019-0 | 1/2001 |
| WO | WO-03/020742-0 | 3/2003 |

OTHER PUBLICATIONS

Sato, H., et al., 1991, Identification and mapping of neutralizing epitopes of human parvovirus B19 by using human antibodies, J. Virol. 65(10):5485-5490.*
Smith, D. B and L. M. Corcoran, 1994, Expression and purification of glutathione-S-transferase fusion proteins, Curr. Prot. Mol. Biol. 16.7. 1-16.7.7.*
Nguyen, Q. T., et al., 1999, Novel human erythrovirus associated with transient aplastic anemia, J. Clin. Microbiol. 37(8):2483-2487.*
Heegaard, E. D., et al., 2002, Baculovirus expression of erythrovirus V9 capsids and screening by ELISA: serologic cross-reactivity with erythrovirus B19, J. Med. Virol. 66:246-252.*
Japanese Office Action dated Mar. 2, 2010 for Japanese Application No. 2000-523317.
Aberham et al., A Quantitative, internally controlled real-time PCR Assay for the detection of parvovirus B19 DNA Journal of Virological Methods, 92:183-191, 2001.
Carriere et al., Rapid and sensitive method for the detection of B19 virus DNA using the polymerase chain reaction with nested primers Journal of Virological Methods, 44:221-234, 1993.
Durigon et al., Multiple primer pairs for polymerase chain reaction (PCR) amplification of human parvovirus B19 DNA Journal of Virological Methods, 44:155-165, 1993.
Extended European Search report for EPO Patent Application No. 05 79 5432 dated Jan. 30, 2009.
Harder et al., New LightCycler PCR for Rapid and Sensitive Quantification of Parvovirus B19 DNA Guides Therapeutic Decision-Making in Relapsing Infections Journal of Clinical Microbiology, 39:4413-4419, 2001.
Heegaard et al., Novel PCR Assay for Differential Detection and Screening of Erythrovirus B19 and Erythrovirus V9 Journal of Medical Virology, 65:362-367, 2001.
Schalasta et al., LightCycler Consensus PCR for Rapid and Differential Detection of Human Erythrovirus B19 and V9 Isolates Journal of Medical Virology 73:54-59, 2004.
Schmidt et al., Parvovirus B19 DNA in plasma pools and plasma derivatives Vox Sanguinis, 81:228-235, 2001.
Servant et al., Genetic Diversity within Human Erythroviruses: Identification of Three Genotypes Journal of Virology 76:9124-9134, 2002.
Barany, F., Genetic disease detection and DNA amplification using cloned thermostable ligase, Proc. Natl. Acad. Sci. USA, 88:189-193 (1991).
Blackburn, G.F. et al., Electrochemiluminescence Detection for Development of Immunoassays and DNA Probe Assays for Clinical Diagnostics, Clin. Chem., 37:1534-1539 (1991).
Candotti et al., Identification and characterization of persistent human erythrovirus infection in blood donor samples. Journal of Virology, 78(22): 12169-12178, 2004.
Corcoran et al., Letter to the Editor: Evidence of serological cross-reactivity between genotype 1 and genotype 3 erythrovirus infections. Journal of Virology, 79(8): 5238-5239, 2005.
Corcoran et al., Impaired gamma interferon responses against parvovirus B19 by recently infected children. Journal of Virology, 74(21): 9903-9910, 2000.
Corcoran and Doyle, Advances in the biology, disgnosis and host-pathogen interactions of parvovirus B19. Journal of Medical Microbiology, 53:459-475, 2004.

(Continued)

*Primary Examiner* — Jeffrey S. Parkin
(74) *Attorney, Agent, or Firm* — Morgan, Lewis & Bockius LLP

(57) ABSTRACT

The invention relates to nucleic sequences derived from a human erythrovirus type V9, fragments of the sequences and their methods of use including applications as a diagnostic reagent and as immunogenic agent.

10 Claims, 8 Drawing Sheets

OTHER PUBLICATIONS

Cossart et al. Parvovirus-like particles in human sera. The Lancet, Jan. 11, 1975, p. 72-73.

Duck, P. et al., Probe amplifier system Based on Chimeric Cycling Oligonucleotides, Bio-techniques, 9:142-147 (1990).

Ekman et al., Biological and immunological relations among human parvovirus B19 genotypes 1 to 3. Journal of Virology, 81(13): 6927-6935, 2007.

Haruna, I. and S. Spiegelman, Specific Template Requirements of RNA Replicases, Proc. Natl. Acad. Sci. USA, 54:579-587 (1965).

Heegaard et al., Baculovirus expression of erythrovirus V9 capsids and screening by ELISA: serologic cross-reactivity with erythrovirus B19. *J Med Virol.* 66(2):246-52, 2002.

Hemauer, A. et al., Sequence Variability Among Different Parovirus B19 Isolates, Journal of General Virology, vol. 77, pp. 1781-1795, (1996).

Hicks K. E. et al., Sequence Analysis of a Pavovirus B19 Isolate Baculovirus Expression of the Non-Structural Problem, Archives of Virology, vol. 141, pp. 1319-1327, (1996).

Hokynar et al., Biological and immunological relation of the three variants of human parvovirus B19, Xith Parvovirus Conference, Aug. 27-31, 2006 Les Diablerets, Switzerland.

Hokynar et al., Rapid Communication: A New parvovirus genotype persistent in the human skin. Virology, 302:224-228, 2002.

Lefrere, J.J. et al., Albumin batches and B19 parvovirus DNA, Transfusion, 35:389-391 (1995).

Nguyen et al., Detection of an Erythrovirus Sequence Distinct from B19 in a Child with Acute Anemia, The Lancet, vol. 352, No. 9139, p. 1524, Nov. 1998.

Nguyen et al., Identification and characterization of a second novel human erythrovirus variant, A6. Virology, 301: 374-380, 2002.

Parsyan et al., Reactivity of genotype-specific recombinant proteins of human erythrovirus B19 with plasmas from areas where genotype 1 or 3 is endemic. Journal of Clinical Microbiology, 44(4): 1367-1375, 2006.

Saiki, R.K. et al., Analysis of enzymatically amplified β-globin and HLA-DQα NA with allele-specific oligonucleotide probes, Nature, 324:163-66 (1986).

Servant et al., Genetic diversity within human erythroviruses: Identification of three genotypes. Journal of Virology, 76(18): 9124-9134, 2002.

Shade, R.O. et al., Nucleotide Sequence and Genome Organization of Human Parvovirus B19 Isolated from the Serum of a Child during Aplastic Crisis, J. Viral., 58, 3:92 1-93 6, B19—AU (1986).

Wahl, G.M., et al., Molecular hybridization of immobilized nucleic acids: theoretical concepts and practical considerations, Meth, Enzymol. 152:399-407 (1987).

Wallace, R. B. and C. G. Miyada, Oligonucleotide probes for the screening of recombinant DNA libraries, Meth. Enzymol., 152:432-442 (1987).

Control Authority Batch Release of Blood Products, 2007. OMCL Guideline for validation of nucleic acid amplification techniques (NAT) for quantitation of B19 virus DNA in plasma pools.

* cited by examiner

|        | nsvp | aua  | pro  | v9    |
|--------|------|------|------|-------|
| nsvp   | 0.00 | 0.70 | 0.80 | 14.77 |
| pvbaua |      | 0.00 | 0.90 | 15.03 |
| pvbpro |      |      | 0.00 | 15.03 |
| v9     |      |      |      | 0.00  |

FIGURE 4

|            | 420  | 599  | nsvp | 560  | aua  | 528  | pro  | V9    |
|------------|------|------|------|------|------|------|------|-------|
| e09420     | 0.00 | 0.65 | 0.75 | 0.70 | 0.80 | 0.75 | 0.85 | 14.87 |
| pvb19x599  |      | 0.00 | 0.70 | 0.65 | 0.75 | 0.70 | 0.80 | 14.93 |
| pvb19nsvp  |      |      | 0.00 | 0.35 | 0.45 | 0.70 | 0.70 | 14.99 |
| pvb19x560  |      |      |      | 0.00 | 0.40 | 0.65 | 0.65 | 14.98 |
| pvbaua     |      |      |      |      | 0.00 | 0.75 | 0.75 | 15.06 |
| pvb19x528  |      |      |      |      |      | 0.00 | 0.80 | 15.17 |
| pvbpro     |      |      |      |      |      |      | 0.00 | 15.11 |
| V9         |      |      |      |      |      |      |      | 0.00  |

FIGURE 5

| | 510 | 511 | 514 | 515 | 528 | 513 | nsvp | 358 | 517 | 508 | 512 | 420 | 516 | aua | 560 | 518 | 546 | pro | 599 | 509 | 506 | 507 | v9 |
|---|---|---|---|---|---|---|---|---|---|---|---|---|---|---|---|---|---|---|---|---|---|---|---|
| ebu38510 | 0.00 | 0.56 | 0.99 | 0.95 | 0.99 | 0.99 | 0.90 | 0.95 | 0.82 | 1.08 | 0.86 | 1.21 | 1.03 | 0.95 | 0.95 | 0.95 | 1.16 | 1.21 | 1.29 | 1.82 | 3.73 | 4.59 | 12.69 |
| ebu38511 | | 0.00 | 0.77 | 0.90 | 0.95 | 0.95 | 0.86 | 0.82 | 0.69 | 0.95 | 0.82 | 1.08 | 0.90 | 0.82 | 0.82 | 0.82 | 0.95 | 1.08 | 1.16 | 1.69 | 3.64 | 4.64 | 12.74 |
| ebu38514 | | | 0.00 | 0.99 | 0.95 | 1.03 | 0.95 | 0.82 | 0.77 | 0.95 | 0.90 | 1.16 | 0.86 | 0.82 | 0.82 | 0.82 | 1.03 | 1.16 | 1.08 | 1.69 | 3.73 | 4.77 | 13.01 |
| ebu38515 | | | | 0.00 | 0.47 | 0.99 | 0.90 | 0.86 | 0.82 | 0.90 | 0.77 | 1.03 | 0.82 | 0.77 | 0.77 | 0.77 | 0.99 | 0.95 | 1.08 | 1.64 | 3.73 | 4.59 | 12.95 |
| pvb19x528 | | | | | 0.00 | 0.95 | 0.86 | 0.90 | 0.77 | 0.86 | 0.82 | 1.08 | 0.82 | 0.73 | 0.73 | 0.73 | 0.95 | 0.99 | 1.03 | 1.60 | 3.64 | 4.64 | 12.85 |
| ebu38513 | | | | | | 0.00 | 0.86 | 0.99 | 0.77 | 0.86 | 0.82 | 1.16 | 0.82 | 0.73 | 0.73 | 0.73 | 0.95 | 1.03 | 1.16 | 1.69 | 3.64 | 4.77 | 12.85 |
| pvb19nsvp | | | | | | | 0.51 | 0.90 | 0.69 | 0.77 | 0.64 | 1.12 | 0.86 | 0.77 | 0.77 | 0.77 | 0.99 | 0.82 | 1.08 | 1.55 | 3.41 | 4.46 | 12.69 |
| bvu31358 | | | | | | | | 0.00 | 0.47 | 0.90 | 0.86 | 0.99 | 0.73 | 0.64 | 0.64 | 0.73 | 0.77 | 1.03 | 1.12 | 1.69 | 3.78 | 4.50 | 13.01 |
| ebu38517 | | | | | | | | | 0.00 | 0.77 | 0.73 | 0.82 | 0.69 | 0.60 | 0.64 | 0.64 | 0.86 | 0.99 | 0.99 | 1.55 | 3.64 | 4.50 | 12.90 |
| ebu38508 | | | | | | | | | | 0.00 | 0.77 | 0.99 | 0.73 | 0.64 | 0.60 | 0.69 | 0.73 | 0.69 | 0.77 | 1.42 | 3.55 | 4.50 | 13.12 |
| ebu38512 | | | | | | | | | | | 0.00 | 0.73 | 0.69 | 0.60 | 0.60 | 0.64 | 0.64 | 0.90 | 0.86 | 1.38 | 3.41 | 4.36 | 12.95 |
| e09420 | | | | | | | | | | | | 0.00 | 1.03 | 0.95 | 0.95 | 0.95 | 1.08 | 1.08 | 1.12 | 1.73 | 3.82 | 4.78 | 13.17 |
| ebu38516 | | | | | | | | | | | | | 0.00 | 0.51 | 0.60 | 0.69 | 0.73 | 0.95 | 0.95 | 1.51 | 3.64 | 4.64 | 13.12 |
| pvbaua | | | | | | | | | | | | | | 0.00 | 0.51 | 0.60 | 0.64 | 0.86 | 0.86 | 1.34 | 3.55 | 4.50 | 12.90 |
| pvb19x560 | | | | | | | | | | | | | | | 0.00 | 0.60 | 0.73 | 0.95 | 0.95 | 1.47 | 3.41 | 4.55 | 13.05 |
| ebu38518 | | | | | | | | | | | | | | | | 0.00 | 0.82 | 0.86 | 0.95 | 1.47 | 3.82 | 4.36 | 12.95 |
| ebu38546 | | | | | | | | | | | | | | | | | 0.00 | 0.95 | 0.99 | 1.55 | 3.37 | 4.64 | 13.16 |
| pvbpro | | | | | | | | | | | | | | | | | | 0.00 | 0.90 | 1.16 | 3.68 | 4.46 | 13.00 |
| pvb19x599 | | | | | | | | | | | | | | | | | | | 0.00 | 1.12 | 3.64 | 4.68 | 13.01 |
| ebu38509 | | | | | | | | | | | | | | | | | | | | 0.00 | 3.64 | 4.64 | 12.64 |
| ebu38506 | | | | | | | | | | | | | | | | | | | | | 0.00 | 3.51 | 13.11 |
| ebu38507 | | | | | | | | | | | | | | | | | | | | | | 0.00 | 13.47 |
| V9C | | | | | | | | | | | | | | | | | | | | | | | 0.00 |

FIGURE 6

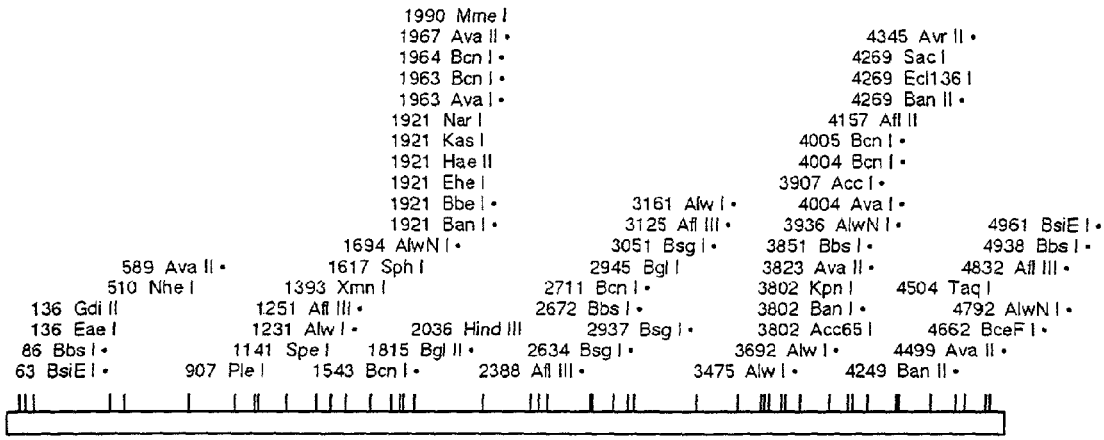
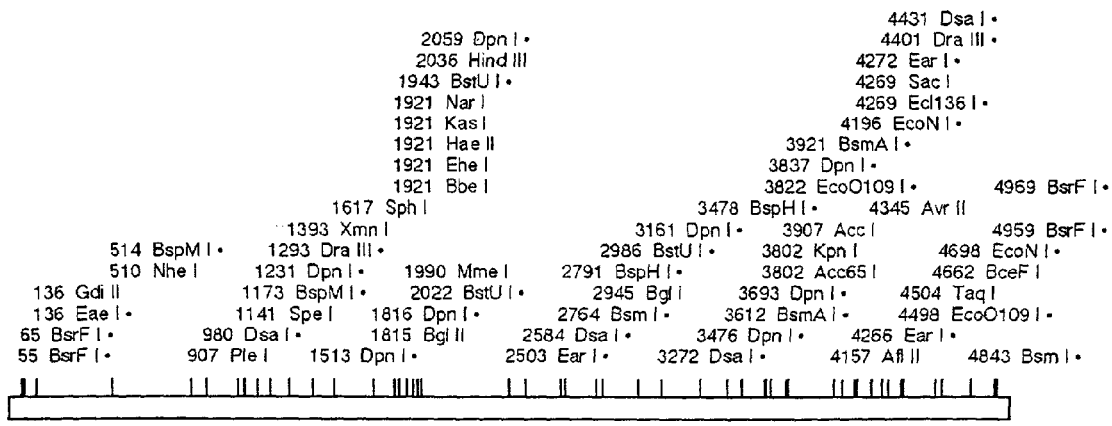
FIGURE 7.1

FIGURE 7.2

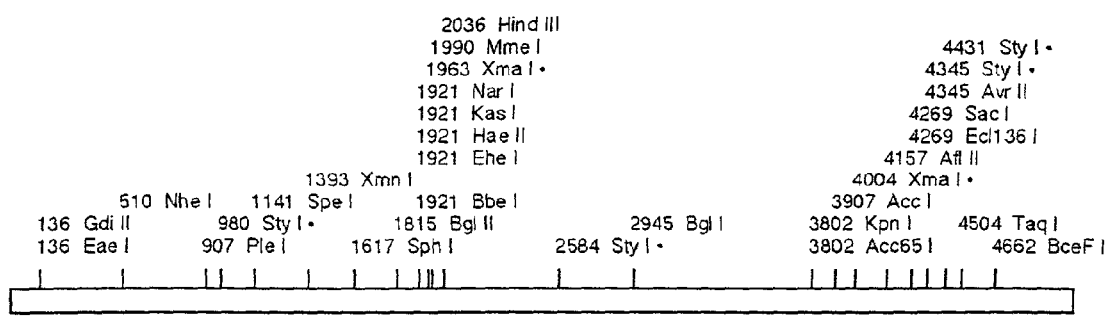
FIGURE 7.3

SEQUENCE LISTING

<160> NUMBER OF SEQ ID NOS: 121

<210> SEQ ID NO 1
<211> LENGTH: 5028
<212> TYPE: DNA
<213> ORGANISM: erythrovirus

<400> SEQUENCE: 1

```
gacgtcacag gaaatgacgt aactgtccgc catcttgtac cggaagtccc gcctaccggc      60
ggcgaccggc ggcatctgat ttggtgtctt cttttttgaaa ttttggcggg cttttttcccg    120 ccttatgcaa ataagcggcc atgtttaatg ttatatttta atttaattgg acaaacgcct     180
aacggttact aggggcggag ttacgggcgg tatataagca gctgcgttcc ctgacacttt     240
cttttctggt tgcttttgac tggaactcac ttgctgttct ttgcctgcta agtaacaggt    300
atttatacta acttttaatt tactaacatg gagctatttc ggggtgtctt gcacatttcc    360
tctaacattc tggactgtgc taatgataac tggtggtgct ctatgctaga cttagatact    420
tctgactggg aaccactaac ccattctaac agattaatgg caatatattt aagcagtgtt    480
gcttctaaac ttgattttac tggggggccg ctagcaggtt gcttatactt ttttcaggtg    540
gaatgtaaca aatttgagga aggctatcat atccatgtag ttattggtgg tccaggacta    600
aatgctagaa acttaactgt gtgcgtagaa ggtttattta ataatgttct ttaccatctt    660
gtaactgaaa gtgttaaact taaatttttg ccagggatga ctaccaaagg aaaatatttt    720
agagatggag agcagtttat agaaaattac ttaatgaaaa aaattccttt aaatgttgtg    780
tggtgtgtaa caaatattga cgggtatata gacacctgta tttccgcctc ttttcggcga    840
ggagcttgtc atgctaaaag accccgcatt actgcaaata cagacagtgc tactaatgaa    900
actggggagt ctagctgtgg aggggagat gttgtgccat tcgctggaaa gggaacaaaa    960
gcggggttaa agtttcaaac catggtaaat tggctatgtg aaaacagagt atttactgaa   1020
gataaatgga aattagtgga ttttaaccaa tatactttat taagtagcag tcacagtggc   1080
agctttcaaa ttcaaagtgc cttaaagtta gctatttata agctactaa cttagtaccc    1140 actagtacat tcttgttaca ttcagacttt gagcaggtta cttgcattaa agaaaataaa   1200
atagtaaaat tattattgtg tcaaaactat gatcctcttt tagtgggtca acatgtgtta   1260
```

```
aggtggattg acaaaaaatg tggtaaaaaa aacaccctgt ggttttacgg gccaccaagt      1320
actggaaaaa caaatttggc aatggctatt gctaaaactg taccagtgta tggaatggtg      1380
aattggaata atgaaaactt tccatttaat gatgtagcgg ggaaaagttt ggtggtctgg      1440
gatgaaggca ttattaagtc cactattgtg aagctgcaa aagccatttt aggtggtcag       1500
ccaaccaggg tagatcagaa aatgcgtggc agtgtggcag tgcccggtgt gcctgtggtt      1560
ataaccagca atggtgacat tacatttgtt gtgagtggta ataccactac aactgtgcat      1620
gctaaagcct taaggaacg gatggtaaag ctaaacttta ccataagatg tagccctgac       1680
atgggtttac ttacagaggc tgatgtacaa caatggctaa cttggtgtaa tgcacaaagc      1740
tggagccact atgaaaactg gcaataaaac tacacatttg atttccctgg aataaatgca      1800
gatgccctcc acccagatct ccaaaccacc cccattgtcc cagacaccag tatcagcagc      1860
agtggtggtg aaagctctga agaactcagt gaaagcagct ttttcaacct catcactcca      1920
ggcgcctgga acagtgaaac cccgcgctct agtacgcccg tccccgggac cagttcagga      1980
gaatcatttg tcggaagccc agtttcctcc gaagtggtag ccgcgtcgtg ggaggaagct      2040
ttttacacgc cgcttgccga tcagtttcgt gaactgttag taggggttga ctttgtatgg      2100
gatggtgtga ggggattgcc tgtttgctgt gtggaacata taaacaacag tggggaggg       2160 ttggggcttt gccctcattg tattaatgtg ggagcttggt ataatggatg gaaatttaga      2220
gagtttactc cagacttagt gcgctgcagt tgtcatgtag gagcctctaa cccatttcct      2280
gtgttaactt gtaaaaaatg tgcttacctg tctggattac aaagttttgt agattatgag      2340
taaaaccact aacaaatggt gggaaagcag tgacaaattt gcccaggacg tgtataagca      2400
gtttgtgcaa ttttatgaaa aagctactgg aacagactta gagcttattc aaattttaaa      2460
agaccattac aacatttctt tagataatcc tttagaaaac ccctcttctt tatttgactt      2520
agttgctcgc attaaaagta atcttaaaaa ctctccagac ctatatagtc atcattttca      2580
gagccatgga cagttatctg accacccccca tgccttatca tccagtaaca gtagtgcaga      2640
acctagagga gaaaatgcag tattatctag tgaagactta cacaagcctg gcaagttag       2700 catacaatta cccggtacta actatgttgg gcctggcaat gagctacaag ctgggcctcc      2760
gcagaatgct gtggacagtg ctgcaaggat tcatgacttt aggtatagcc aattggctaa      2820
gttgggaata aatccttata cacattggac ggtagcagat gaagaattgt taaaaaatat      2880
aaaaaatgaa acagggtttc aagcacaagc agtaaaagat tactttactt taaaaggtgc      2940
agctgcccct gtggcccatt ttcaaggaag tttaccggaa gtgcccgcgt acaacgcctc      3000
agaaaaatac cccagcatga cttcagttaa ctctgcagaa gccagcactg gtgcaggcgg      3060
gggaggtagc aaccctacaa aaagcatgtg gagtgaaggg gctacattta ctgctaattc      3120
tgtaacgtgt acattctcta ggcaattttt aattccatat gatccagagc atcattataa      3180
agtgttctct ccagcagcta gtagctgcca caatgctagt gggaaagagg caaaagtgtg      3240
cactattagt cccattatgg ggtactctac tccgtggaga tacttagatt ttaatgcttt      3300
aaatttgttt ttctcaccat tagagtttca gcacttaatt gaaaattatg gtagtatagc      3360
tccagatgct ttaactgtaa ctatttcaga aattgctgta aaagatgtca cagacaaaac      3420
aggaggaggt gtgcaagtta ctgacagcac cacaggacgt ttgtgtatgt tagtggatca      3480
tgagtataaa tacccatatg tgctaggtca gggacaagac acactagctc cagaactgcc      3540 catttggggtt tactttcccc cccagtatgc ttacttaaca gtaggtgaag taaacacaca      3600
aggaatttca ggagacagca aaaaattggc tagtgaagaa tcagcttttt atgtgttaga      3660
```

```
gcacagttca tttgaacttt tgggtacagg gggatctgcc actatgtcct acaaatttcc    3720
agctgtgccc ccagaaaacc tagaaggctg cagccaacat tttatgaaa tgtacaaccc     3780 tttgtacggt tctcgtttag gggtacctga cacattagga ggggacccta aatttagatc    3840
attgacacac gaagaccacg caattcagcc acaaaacttt atgcctgggc cactaataaa    3900
ttcagtgtct accaaagaag gagacaattc taatacaggt gctggaaaag cccttacggg    3960
gcttagtact ggcactagcc aaaacaccag aatttcccta cgccccgggc cagtatctca    4020
gccataccat cactgggaca ctgataaata tgttacagga ataaatgcca tttcacatgg    4080
acaaaccact tatggaaatg ctgaggacaa agagtatcag caaggggtag gaagatttcc    4140
aaatgaaaaa gaacagctta agcagttaca aggtcttaac atgcacacat acttccctaa    4200
taaaggaacc caacaataca cagaccaaat tgaacgccct cttatggtgg gctctgtttg    4260
gaacagaaga gctcttcact atgaaagtca gctgtggagt aaaatcccta acttagatga    4320
cagttttaaa actcaatttg cagccctagg cgggtgggt ttgcatcaac cacccctca    4380 aatattttta aaaatactac cacaaagtgg gccaattgga ggtattaaat ccatgggaat    4440
tactacttta gttcaatatg ctgtgggaat aatgacagtt accatgacct ttaaattggg    4500
acctcgaaag gctactggaa ggtggaatcc ccagcctggc gtttatcctc ctcatgcagc    4560
tggtcattta ccatatgtac tgtatgaccc cacagctaca gatgcaaagc aacaccacag    4620
acacggatat gaaaagcctg aagaattgtg gactgccaaa agccgtgtgc acccattgta    4680
aacattcccc accgtgtcct cagccaggaa ccgtcaccca ccgccacct gtgccgccca    4740 gattatatgt gccccctcca ataccccgta ggcaaccatc tataaaagat acagacgctg    4800
tagaatataa attattaact agatatgaac aacatgtaat tagaatgcta agattatgta    4860
atatgtacac aagtttggaa aaataaaagc cttaaataaa taattcatag tgtatggttc    4920
tttaaaaatt tcaaaagaa gacaccaaat cagatgccgc cggtcgccgc cggtaggcgg    4980
gacttccggt acaagatggc ggacagttac gtcatttcct gtgacgtc               5028

<210> SEQ ID NO 2
<211> LENGTH: 23
<212> TYPE: DNA
<213> ORGANISM: erythrovirus

<400> SEQUENCE: 2
acttctgact gggaaccact aac                                              23

<210> SEQ ID NO 3
<211> LENGTH: 29
<212> TYPE: DNA
<213> ORGANISM: erythrovirus

<400> SEQUENCE: 3
tttagagatg gagagcagtt tatagaaaa                                        29

<210> SEQ ID NO 4
<211> LENGTH: 35
<212> TYPE: DNA
<213> ORGANISM: erythrovirus

<400> SEQUENCE: 4
tggaataatg aaaactttcc atttaatgat gtagc                                 35

<210> SEQ ID NO 5
<211> LENGTH: 20
<212> TYPE: DNA
```

```
<213> ORGANISM: erythrovirus

<400> SEQUENCE: 5
ttggtggtct gggatgaagg                                              20

<210> SEQ ID NO 6
<211> LENGTH: 20
<212> TYPE: DNA
<213> ORGANISM: erythrovirus

<400> SEQUENCE: 6
acagaggctg atgtacaaca                                              20

<210> SEQ ID NO 7
<211> LENGTH: 21
<212> TYPE: DNA
<213> ORGANISM: erythrovirus

<400> SEQUENCE: 7
tggtgtaatg cacaaagctg g                                            21

<210> SEQ ID NO 8
<211> LENGTH: 31
<212> TYPE: DNA
<213> ORGANISM: erythrovirus

<400> SEQUENCE: 8
ccactatgaa aactgggcaa taaactacac a                                 31

<210> SEQ ID NO 9
<211> LENGTH: 17
<212> TYPE: DNA
<213> ORGANISM: erythrovirus

<400> SEQUENCE: 9
tttgatttcc ctggaat                                                 17

<210> SEQ ID NO 10
<211> LENGTH: 23
<212> TYPE: DNA
<213> ORGANISM: erythrovirus

<400> SEQUENCE: 10
aatgcagatg ccctccaccc aga                                          23

<210> SEQ ID NO 11
<211> LENGTH: 64
<212> TYPE: DNA
<213> ORGANISM: erythrovirus

<400> SEQUENCE: 11
cagacaccag tatcagcagc agtggtggtg aaagctctga gaactcagt gaaagcagct   60 tttt                                                               64

<210> SEQ ID NO 12
<211> LENGTH: 25
<212> TYPE: DNA
<213> ORGANISM: erythrovirus

<400> SEQUENCE: 12
tgaaaccccg cgctctagta cgccc                                        25

<210> SEQ ID NO 13
```

-continued

<211> LENGTH: 55
<212> TYPE: DNA
<213> ORGANISM: erythrovirus

<400> SEQUENCE: 13
tccccgggac cagttcagga gaatcatttg tcggaagccc agtttcctcc gaagt         55

<210> SEQ ID NO 14
<211> LENGTH: 20
<212> TYPE: DNA
<213> ORGANISM: erythrovirus

<400> SEQUENCE: 14
cagtttcgtg aactgttagt                                                20

<210> SEQ ID NO 15
<211> LENGTH: 24
<212> TYPE: DNA
<213> ORGANISM: erythrovirus

<400> SEQUENCE: 15
gcttggtata atggatggaa attt                                           24

<210> SEQ ID NO 16
<211> LENGTH: 26
<212> TYPE: DNA
<213> ORGANISM: erythrovirus

<400> SEQUENCE: 16
aaaaaatgtg cttacctgtc tggatt                                         26

<210> SEQ ID NO 17
<211> LENGTH: 18
<212> TYPE: DNA
<213> ORGANISM: erythrovirus

<400> SEQUENCE: 17
cttaaaaact ctccagac                                                  18

<210> SEQ ID NO 18
<211> LENGTH: 19
<212> TYPE: DNA
<213> ORGANISM: erythrovirus

<400> SEQUENCE: 18
tatatagtca tcattttca                                                 19

<210> SEQ ID NO 19
<211> LENGTH: 43
<212> TYPE: DNA
<213> ORGANISM: erythrovirus

<400> SEQUENCE: 19
catggacagt tatctgacca cccccatgcc ttatcatcca gta                      43

<210> SEQ ID NO 20
<211> LENGTH: 19
<212> TYPE: DNA
<213> ORGANISM: erythrovirus

<400> SEQUENCE: 20
tgcagaacct agaggagaa                                                 19

<210> SEQ ID NO 21

```
<211> LENGTH: 47
<212> TYPE: DNA
<213> ORGANISM: erythrovirus

<400> SEQUENCE: 21
atgcagtatt atctagtgaa gacttacaca agcctgggca agttagc         47

<210> SEQ ID NO 22
<211> LENGTH: 49
<212> TYPE: DNA
<213> ORGANISM: erythrovirus

<400> SEQUENCE: 22
tacccggtac taactatgtt gggcctggca atgagctaca agctgggcc       49

<210> SEQ ID NO 23
<211> LENGTH: 39
<212> TYPE: DNA
<213> ORGANISM: erythrovirus

<400> SEQUENCE: 23
gacagtgctg caaggattca tgactttagg tatagccaa                  39

<210> SEQ ID NO 24
<211> LENGTH: 22
<212> TYPE: DNA
<213> ORGANISM: erythrovirus

<400> SEQUENCE: 24
tggctaagtt gggaataaat cc                                    22

<210> SEQ ID NO 25
<211> LENGTH: 23
<212> TYPE: DNA
<213> ORGANISM: erythrovirus

<400> SEQUENCE: 25
ttaaaaaata taaaaaatga aac                                   23

<210> SEQ ID NO 26
<211> LENGTH: 53
<212> TYPE: DNA
<213> ORGANISM: erythrovirus

<400> SEQUENCE: 26
tactttactt taaaaggtgc agctgccccct gtggcccatt ttcaaggaag ttt 53

<210> SEQ ID NO 27
<211> LENGTH: 23
<212> TYPE: DNA
<213> ORGANISM: erythrovirus

<400> SEQUENCE: 27
tacaacgcct cagaaaaata ccc                                   23

<210> SEQ ID NO 28
<211> LENGTH: 26
<212> TYPE: DNA
<213> ORGANISM: erythrovirus

<400> SEQUENCE: 28
tctgcagaag ccagcactgg tgcagg                                26

<210> SEQ ID NO 29
```

```
<211> LENGTH: 23
<212> TYPE: DNA
<213> ORGANISM: erythrovirus

<400> SEQUENCE: 29
ttagatttta atgctttaaa ttt                                           23

<210> SEQ ID NO 30
<211> LENGTH: 32
<212> TYPE: DNA
<213> ORGANISM: erythrovirus

<400> SEQUENCE: 30
ttagagtttc agcacttaat tgaaaattat gg                                 32

<210> SEQ ID NO 31
<211> LENGTH: 20
<212> TYPE: DNA
<213> ORGANISM: erythrovirus

<400> SEQUENCE: 31
acaggaataa atgccatttc                                               20

<210> SEQ ID NO 32
<211> LENGTH: 24
<212> TYPE: DNA
<213> ORGANISM: erythrovirus

<400> SEQUENCE: 32
gacaaagagt atcagcaagg ggta                                          24

<210> SEQ ID NO 33
<211> LENGTH: 26
<212> TYPE: DNA
<213> ORGANISM: erythrovirus

<400> SEQUENCE: 33
agatttccaa atgaaaaaga acagct                                        26

<210> SEQ ID NO 34
<211> LENGTH: 18
<212> TYPE: DNA
<213> ORGANISM: erythrovirus

<400> SEQUENCE: 34
tcagctgtgg agtaaaat                                                 18

<210> SEQ ID NO 35
<211> LENGTH: 23
<212> TYPE: DNA
<213> ORGANISM: erythrovirus

<400> SEQUENCE: 35
ttagatgaca gttttaaaac tca                                           23

<210> SEQ ID NO 36
<211> LENGTH: 21
<212> TYPE: DNA
<213> ORGANISM: erythrovirus

<400> SEQUENCE: 36
cctcaaatat ttttaaaaat a                                             21

<210> SEQ ID NO 37
```

```
<211> LENGTH: 34
<212> TYPE: DNA
<213> ORGANISM: erythrovirus

<400> SEQUENCE: 37
taccacaaag tgggccaatt ggaggtatta aatc                              34

<210> SEQ ID NO 38
<211> LENGTH: 23
<212> TYPE: DNA
<213> ORGANISM: erythrovirus

<400> SEQUENCE: 38
atgggaatta ctactttagt tca                                         23

<210> SEQ ID NO 39
<211> LENGTH: 62
<212> TYPE: DNA
<213> ORGANISM: erythrovirus

<400> SEQUENCE: 39
ggtcatttac catatgtact gtatgacccc acagctacag atgcaaagca acaccacaga  60
ca                                                                62

<210> SEQ ID NO 40
<211> LENGTH: 29
<212> TYPE: DNA
<213> ORGANISM: erythrovirus

<400> SEQUENCE: 40
ggatatgaaa agcctgaaga attgtggac                                   29

<210> SEQ ID NO 41
<211> LENGTH: 30
<212> TYPE: DNA
<213> ORGANISM: erythrovirus

<400> SEQUENCE: 41
gccaaaagcc gtgtgcaccc attgtaaaca                                  30

<210> SEQ ID NO 42
<211> LENGTH: 21
<212> TYPE: DNA
<213> ORGANISM: erythrovirus

<400> SEQUENCE: 42
tccccaccgt gtcctcagcc a                                           21

<210> SEQ ID NO 43
<211> LENGTH: 109
<212> TYPE: DNA
<213> ORGANISM: erythrovirus

<400> SEQUENCE: 43
ctttaaaaat ttcaaaaaga agacaccaaa tcagatgccg ccggtcgccg ccggtaggcg  60
ggacttccgg tacaagatgg cggacagtta cgtcatttcc tgtgacgtc             109

<210> SEQ ID NO 44
<211> LENGTH: 103
<212> TYPE: DNA
<213> ORGANISM: erythrovirus

<400> SEQUENCE: 44
```

```
gacgtcacag gaaatgacgt aactgtccgc catcttgtac cggaagtccc gcctaccggc    60
ggcgaccggc ggcatctgat ttggtgtctt cttttgaaa ttt                      103
```

```
<210> SEQ ID NO 45
<211> LENGTH: 210
<212> TYPE: DNA
<213> ORGANISM: erythrovirus

<400> SEQUENCE: 45 cttttgaaa ttttggcggg ctttttcccg ccttatgcaa ataagcggcc atgtttaatg    60
ttatatttta atttaattgg acaaacgcct aacggttact aggggcggag ttacgggcgg   120
tatataagca gctgcgttcc ctgacacttt cttttctggt tgcttttgac tggaactcac   180
ttgctgttct ttgcctgcta agtaacaggt                                    210
```

```
<210> SEQ ID NO 46
<211> LENGTH: 30
<212> TYPE: DNA
<213> ORGANISM: erythrovirus

<400> SEQUENCE: 46
atttatacta acttttaatt tactaacatg                                     30
```

```
<210> SEQ ID NO 47
<211> LENGTH: 100
<212> TYPE: DNA
<213> ORGANISM: erythrovirus

<400> SEQUENCE: 47
gagctatttc ggggtgtctt gcacatttcc tctaacattc tggactgtgc taatgataac    60
tggtggtgct ctatgctaga cttagatact tctgactggg                         100
```

```
<210> SEQ ID NO 48
<211> LENGTH: 117
<212> TYPE: DNA
<213> ORGANISM: erythrovirus

<400> SEQUENCE: 48
aaccactaac ccattctaac agattaatgg caatatattt aagcagtgtt gcttctaaac    60
ttgattttac tgggggccg ctagcaggtt gcttatactt ttttcaggtg gaatgta       117
```

```
<210> SEQ ID NO 49
<211> LENGTH: 183
<212> TYPE: DNA
<213> ORGANISM: erythrovirus

<400> SEQUENCE: 49
acaaatttga ggaaggctat catatccatg tagttattgg tggtccagga ctaaatgcta    60
gaaacttaac tgtgtgcgta gaaggtttat ttaataatgt tctttaccat cttgtaactg   120
aaagtgttaa acttaaattt ttgccaggga tgactaccaa aggaaaatat tttagagatg   180
gag                                                                  183
```

```
<210> SEQ ID NO 50
<211> LENGTH: 670
<212> TYPE: DNA
<213> ORGANISM: erythrovirus

<400> SEQUENCE: 50
agcagtttat agaaaattac ttaatgaaaa aaattccttt aaatgttgtg tggtgtgtaa    60
```

```
caaatattga cgggtatata gacacctgta tttccgcctc ttttcggcga ggagcttgtc      120
atgctaaaag accccgcatt actgcaaata cagacagtgc tactaatgaa actggggagt      180
ctagctgtgg aggggagat gttgtgccat tcgctggaaa gggaacaaaa gcggggttaa       240
agtttcaaac catggtaaat tggctatgtg aaaacagagt atttactgaa gataaatgga      300
aattagtgga ttttaaccaa tatactttat taagtagcag tcacagtggc agctttcaaa      360
ttcaaagtgc cttaaagtta gctatttata aagctactaa cttagtaccc actagtacat      420
tcttgttaca ttcagacttt gagcaggtta cttgcattaa agaaaataaa atagtaaaat      480
tattattgtg tcaaaactat gatcctcttt tagtgggtca acatgtgtta aggtggattg      540
acaaaaaatg tggtaaaaaa aacaccctgt ggttttacgg gccaccaagt actggaaaaa      600
caaatttggc aatggctatt gctaaaactg taccagtgta tggaatggtg aattggaata      660
atgaaaactt                                                              670

<210> SEQ ID NO 51
<211> LENGTH: 36
<212> TYPE: DNA
<213> ORGANISM: erythrovirus

<400> SEQUENCE: 51
tccatttaat gatgtagcgg ggaaaagttt ggtggt                                  36

<210> SEQ ID NO 52
<211> LENGTH: 46
<212> TYPE: DNA
<213> ORGANISM: erythrovirus

<400> SEQUENCE: 52
ctgggatgaa ggcattatta agtccactat tgtggaagct gcaaaa                       46

<210> SEQ ID NO 53
<211> LENGTH: 84
<212> TYPE: DNA
<213> ORGANISM: erythrovirus

<400> SEQUENCE: 53
gccattttag gtggtcagcc aaccagggta gatcagaaaa tgcgtggcag tgtggcagtg       60
cccggtgtgc ctgtggttat aacc                                              84

<210> SEQ ID NO 54
<211> LENGTH: 60
<212> TYPE: DNA
<213> ORGANISM: erythrovirus

<400> SEQUENCE: 54
agcaatggtg acattacatt tgttgtgagt ggtaatacca ctacaactgt gcatgctaaa       60

<210> SEQ ID NO 55
<211> LENGTH: 76
<212> TYPE: DNA
<213> ORGANISM: erythrovirus

<400> SEQUENCE: 55
gccttaaagg aacggatggt aaagctaaac tttaccataa gatgtagccc tgacatgggt       60
ttacttacag aggctg                                                       76

<210> SEQ ID NO 56
<211> LENGTH: 30
<212> TYPE: DNA
```

<213> ORGANISM: erythrovirus

<400> SEQUENCE: 56
atgtacaaca atggctaact tggtgtaatg 30

<210> SEQ ID NO 57
<211> LENGTH: 28
<212> TYPE: DNA
<213> ORGANISM: erythrovirus

<400> SEQUENCE: 57
cacaaagctg gagccactat gaaaactg 28

<210> SEQ ID NO 58
<211> LENGTH: 98
<212> TYPE: DNA
<213> ORGANISM: erythrovirus

<400> SEQUENCE: 58
ttcaggagaa tcatttgtcg gaagcccagt ttcctccgaa gtggtagccg cgtcgtggga 60
ggaagctttt tacacgccgc ttgccgatca gtttcgtg 98

<210> SEQ ID NO 59
<211> LENGTH: 134
<212> TYPE: DNA
<213> ORGANISM: erythrovirus

<400> SEQUENCE: 59
aactgttagt aggggttgac tttgtatggg atggtgtgag gggattgcct gtttgctgtg 60
tggaacatat aaacaacagt gggggagggt tggggctttg ccctcattgt attaatgtgg 120
gagcttggta taat 134

<210> SEQ ID NO 60
<211> LENGTH: 100
<212> TYPE: DNA
<213> ORGANISM: erythrovirus

<400> SEQUENCE: 60
ggatggaaat ttagagagtt tactccagac ttagtgcgct gcagttgtca tgtaggagcc 60
tctaacccat tttctgtgtt aacttgtaaa aatgtgctt 100

<210> SEQ ID NO 61
<211> LENGTH: 30
<212> TYPE: DNA
<213> ORGANISM: erythrovirus

<400> SEQUENCE: 61
acctgtctgg attacaaagt tttgtagatt 30

<210> SEQ ID NO 62
<211> LENGTH: 102
<212> TYPE: DNA
<213> ORGANISM: erythrovirus

<400> SEQUENCE: 62
atgagtaaaa ccactaacaa atggtgggaa agcagtgaca aatttgccca ggacgtgtat 60
aagcagtttg tgcaatttta tgaaaaagct actggaacag ac 102

<210> SEQ ID NO 63
<211> LENGTH: 114
<212> TYPE: DNA

-continued

```
<213> ORGANISM: erythrovirus

<400> SEQUENCE: 63
ttagagctta ttcaaatttt aaaagaccat tacaacattt ctttagataa tcctttagaa      60
aacccctctt ctttatttga cttagttgct cgcattaaaa gtaatcttaa aaac          114

<210> SEQ ID NO 64
<211> LENGTH: 22
<212> TYPE: DNA
<213> ORGANISM: erythrovirus

<400> SEQUENCE: 64
tctccagacc tatatagtca tc                                              22

<210> SEQ ID NO 65
<211> LENGTH: 23
<212> TYPE: DNA
<213> ORGANISM: erythrovirus

<400> SEQUENCE: 65
attttcagag ccatggacag tta                                             23

<210> SEQ ID NO 66
<211> LENGTH: 30
<212> TYPE: DNA
<213> ORGANISM: erythrovirus

<400> SEQUENCE: 66
atcatccagt aacagtagtg cagaacctag                                      30

<210> SEQ ID NO 67
<211> LENGTH: 39
<212> TYPE: DNA
<213> ORGANISM: erythrovirus

<400> SEQUENCE: 67
caagctgggc ctccgcagaa tgctgtggac agtgctgca                            39

<210> SEQ ID NO 68
<211> LENGTH: 56
<212> TYPE: DNA
<213> ORGANISM: erythrovirus

<400> SEQUENCE: 68
ggaataaatc cttatacaca ttggacggta gcagatgaag aattgttaaa aaatat         56

<210> SEQ ID NO 69
<211> LENGTH: 51
<212> TYPE: DNA
<213> ORGANISM: erythrovirus

<400> SEQUENCE: 69
aaaaaatgaa acagggtttc aagcacaagc agtaaaagat tactttactt t              51

<210> SEQ ID NO 70
<211> LENGTH: 37
<212> TYPE: DNA
<213> ORGANISM: erythrovirus

<400> SEQUENCE: 70
aaggaagttt accggaagtg cccgcgtaca acgcctc                              37

<210> SEQ ID NO 71
```

```
<211> LENGTH: 42
<212> TYPE: DNA
<213> ORGANISM: erythrovirus

<400> SEQUENCE: 71
agaaaaatac cccagcatga cttcagttaa ctctgcagaa gc                          42

<210> SEQ ID NO 72
<211> LENGTH: 255
<212> TYPE: DNA
<213> ORGANISM: erythrovirus

<400> SEQUENCE: 72
cagcactggt gcaggcgggg gaggtagcaa ccctacaaaa agcatgtgga gtgaaggggc       60
tacatttact gctaattctg taacgtgtac attctctagg caattttttaa ttccatatga    120 tccagagcat cattataaag tgttctctcc agcagctagt agctgccaca atgctagtgg    180
gaaagaggca aaagtgtgca ctattagtcc cattatgggg tactctactc cgtggagata    240
cttagatttt aatgc                                                       255

<210> SEQ ID NO 73
<211> LENGTH: 33
<212> TYPE: DNA
<213> ORGANISM: erythrovirus

<400> SEQUENCE: 73
tttaaatttg tttttctcac cattagagtt tca                                    33

<210> SEQ ID NO 74
<211> LENGTH: 725
<212> TYPE: DNA
<213> ORGANISM: erythrovirus

<400> SEQUENCE: 74
gaaaattatg gtagtatagc tccagatgct ttaactgtaa ctatttcaga aattgctgta      60
aaagatgtca cagacaaaac aggaggaggt gtgcaagtta ctgacagcac cacaggacgt    120
ttgtgtatgt tagtggatca tgagtataaa tacccatatg tgctaggtca gggacaagac    180
acactagctc cagaactgcc catttgggtt tactttcccc cccagtatgc ttacttaaca    240
gtaggtgaag taaacacaca aggaatttca ggagacagca aaaaattggc tagtgaagaa    300
tcagcttttt atgtgttaga gcacagttca tttgaacttt tgggtacagg gggatctgcc    360
actatgtcct acaaatttcc agctgtgccc ccagaaaaacc tagaaggctg cagccaacat    420
ttttatgaaa tgtacaaccc tttgtacggt tctcgtttag gggtacctga cacattagga    480
ggggacccta aatttagatc attgacacac gaagaccacg caattcagcc acaaaacttt    540
atgcctgggc cactaataaa ttcagtgtct accaaagaag gagacaattc taatacaggt    600
gctggaaaag cccttacggg gcttagtact ggcactagcc aaaacaccag aatttcccta    660
cgccccgggc cagtatctca gccataccat cactgggaca ctgataaata tgttacagga    720
ataaa                                                                  725

<210> SEQ ID NO 75
<211> LENGTH: 49
<212> TYPE: DNA
<213> ORGANISM: erythrovirus

<400> SEQUENCE: 75
tgccatttca catggacaaa ccacttatgg aaatgctgag gacaaagag                   49
```

-continued

<210> SEQ ID NO 76
<211> LENGTH: 30
<212> TYPE: DNA
<213> ORGANISM: erythrovirus

<400> SEQUENCE: 76
tatcagcaag gggtaggaag atttccaaat                                    30

<210> SEQ ID NO 77
<211> LENGTH: 180
<212> TYPE: DNA
<213> ORGANISM: erythrovirus

<400> SEQUENCE: 77
gaaaaagaac agcttaagca gttacaaggt cttaacatgc acacatactt ccctaataaa   60
ggaacccaac aatacacaga ccaaattgaa cgccctctta tggtgggctc tgtttggaac  120
agaagagctc ttcactatga aagtcagctg tggagtaaaa tccctaactt agatgacagt  180

<210> SEQ ID NO 78
<211> LENGTH: 64
<212> TYPE: DNA
<213> ORGANISM: erythrovirus

<400> SEQUENCE: 78
tttaaaactc aatttgcagc cctaggcggg tggggtttgc atcaaccacc ccctcaaata   60
tttt                                                                64

<210> SEQ ID NO 79
<211> LENGTH: 152
<212> TYPE: DNA
<213> ORGANISM: erythrovirus

<400> SEQUENCE: 79
aggtattaaa tccatgggaa ttactacttt agttcaatat gctgtgggaa taatgacagt   60
taccatgacc tttaaattgg gacctcgaaa ggctactgga aggtggaatc cccagcctgg  120
cgtttatcct cctcatgcag ctggtcattt ac                                152

<210> SEQ ID NO 80
<211> LENGTH: 260
<212> TYPE: DNA
<213> ORGANISM: erythrovirus

<400> SEQUENCE: 80
cccattgtaa acattcccca ccgtgtcctc agccaggaac cgtcacccac cgcccacctg   60
tgccgcccag attatatgtg ccccctccaa taccccgtag caaccatct ataaaagata   120 cagacgctgt agaatataaa ttattaacta gatatgaaca acatgtaatt agaatgctaa  180
gattatgtaa tatgtacaca agtttggaaa aataaaagcc ttaaataaat aattcatagt  240
gtatggttct ttaaaaattt                                              260

<210> SEQ ID NO 81
<211> LENGTH: 2013
<212> TYPE: DNA
<213> ORGANISM: erythrovirus
<220> FEATURE:
<221> NAME/KEY: CDS
<222> LOCATION: (1)..(2013)

<400> SEQUENCE: 81 atg gag cta ttt cgg ggt gtc ttg cac att tcc tct aac att ctg gac   48

```
                    -continued

Met Glu Leu Phe Arg Gly Val Leu His Ile Ser Ser Asn Ile Leu Asp
1               5                   10                  15 tgt gct aat gat aac tgg tgg tgc tct atg cta gac tta gat act tct    96
Cys Ala Asn Asp Asn Trp Trp Cys Ser Met Leu Asp Leu Asp Thr Ser
            20                  25                  30 gac tgg gaa cca cta acc cat tct aac aga tta atg gca ata tat tta   144
Asp Trp Glu Pro Leu Thr His Ser Asn Arg Leu Met Ala Ile Tyr Leu
        35                  40                  45 agc agt gtt gct tct aaa ctt gat ttt act ggg ggg ccg cta gca ggt   192
Ser Ser Val Ala Ser Lys Leu Asp Phe Thr Gly Gly Pro Leu Ala Gly
50                  55                  60 tgc tta tac ttt ttt cag gtg gaa tgt aac aaa ttt gag gaa ggc tat   240
Cys Leu Tyr Phe Phe Gln Val Glu Cys Asn Lys Phe Glu Glu Gly Tyr
65                  70                  75                  80 cat atc cat gta gtt att ggt ggt cca gga cta aat gct aga aac tta   288
His Ile His Val Val Ile Gly Gly Pro Gly Leu Asn Ala Arg Asn Leu
            85                  90                  95 act gtg tgc gta gaa ggt tta ttt aat aat gtt ctt tac cat ctt gta   336
Thr Val Cys Val Glu Gly Leu Phe Asn Asn Val Leu Tyr His Leu Val
        100                 105                 110 act gaa agt gtt aaa ctt aaa ttt ttg cca ggg atg act acc aaa gga   384
Thr Glu Ser Val Lys Leu Lys Phe Leu Pro Gly Met Thr Thr Lys Gly
        115                 120                 125 aaa tat ttt aga gat gga gag cag ttt ata gaa aat tac tta atg aaa   432
Lys Tyr Phe Arg Asp Gly Glu Gln Phe Ile Glu Asn Tyr Leu Met Lys
    130                 135                 140 aaa att cct tta aat gtt gtg tgg tgt gta aca aat att gac ggg tat   480
Lys Ile Pro Leu Asn Val Val Trp Cys Val Thr Asn Ile Asp Gly Tyr
145                 150                 155                 160 ata gac acc tgt att tcc gcc tct ttt cgg cga gga gct tgt cat gct   528
Ile Asp Thr Cys Ile Ser Ala Ser Phe Arg Arg Gly Ala Cys His Ala
                165                 170                 175 aaa aga ccc cgc att act gca aat aca gac agt gct act aat gaa act   576
Lys Arg Pro Arg Ile Thr Ala Asn Thr Asp Ser Ala Thr Asn Glu Thr
            180                 185                 190 ggg gag tct agc tgt gga ggg gga gat gtt gtg cca ttc gct gga aag   624
Gly Glu Ser Ser Cys Gly Gly Gly Asp Val Val Pro Phe Ala Gly Lys
        195                 200                 205 gga aca aaa gcg ggg tta aag ttt caa acc atg gta aat tgg cta tgt   672
Gly Thr Lys Ala Gly Leu Lys Phe Gln Thr Met Val Asn Trp Leu Cys
    210                 215                 220 gaa aac aga gta ttt act gaa gat aaa tgg aaa tta gtg gat ttt aac   720
Glu Asn Arg Val Phe Thr Glu Asp Lys Trp Lys Leu Val Asp Phe Asn
225                 230                 235                 240 caa tat act tta tta agt agc agt cac agt ggc agc ttt caa att caa   768
Gln Tyr Thr Leu Leu Ser Ser Ser His Ser Gly Ser Phe Gln Ile Gln
                245                 250                 255 agt gcc tta aag tta gct att tat aaa gct act aac tta gta ccc act   816
Ser Ala Leu Lys Leu Ala Ile Tyr Lys Ala Thr Asn Leu Val Pro Thr
            260                 265                 270 agt aca ttc ttg tta cat tca gac ttt gag cag gtt act tgc att aaa   864
Ser Thr Phe Leu Leu His Ser Asp Phe Glu Gln Val Thr Cys Ile Lys
        275                 280                 285 gaa aat aaa ata gta aaa tta tta ttg tgt caa aac tat gat cct ctt   912
Glu Asn Lys Ile Val Lys Leu Leu Leu Cys Gln Asn Tyr Asp Pro Leu
    290                 295                 300 tta gtg ggt caa cat gtg tta agg tgg att gac aaa aaa tgt ggt aaa   960
Leu Val Gly Gln His Val Leu Arg Trp Ile Asp Lys Lys Cys Gly Lys
305                 310                 315                 320 aaa aac acc ctg tgg ttt tac ggg cca cca agt act gga aaa aca aat  1008
```

```
                    Lys Asn Thr Leu Trp Phe Tyr Gly Pro Pro Ser Thr Gly Lys Thr Asn
                                    325                 330                 335 ttg gca atg gct att gct aaa act gta cca gtg tat gga atg gtg aat        1056
Leu Ala Met Ala Ile Ala Lys Thr Val Pro Val Tyr Gly Met Val Asn
                340                 345                 350 tgg aat aat gaa aac ttt cca ttt aat gat gta gcg ggg aaa agt ttg        1104
Trp Asn Asn Glu Asn Phe Pro Phe Asn Asp Val Ala Gly Lys Ser Leu
            355                 360                 365 gtg gtc tgg gat gaa ggc att att aag tcc act att gtg gaa gct gca        1152
Val Val Trp Asp Glu Gly Ile Ile Lys Ser Thr Ile Val Glu Ala Ala
        370                 375                 380 aaa gcc att tta ggt ggt cag cca acc agg gta gat cag aaa atg cgt        1200
Lys Ala Ile Leu Gly Gly Gln Pro Thr Arg Val Asp Gln Lys Met Arg
385                 390                 395                 400 ggc agt gtg gca gtg ccc ggt gtg cct gtg gtt ata acc agc aat ggc        1248
Gly Ser Val Ala Val Pro Gly Val Pro Val Val Ile Thr Ser Asn Gly
                405                 410                 415 gac att aca ttt gtt gtg agt ggt aat acc act aca act gtg cat gct        1296
Asp Ile Thr Phe Val Val Ser Gly Asn Thr Thr Thr Thr Val His Ala
                420                 425                 430 aaa gcc tta aag gaa cgg atg gta aag cta aac ttt acc ata aga tgt        1344
Lys Ala Leu Lys Glu Arg Met Val Lys Leu Asn Phe Thr Ile Arg Cys
            435                 440                 445 agc cct gac atg ggt tta ctt aca gag gct gat gta caa caa tgg cta        1392
Ser Pro Asp Met Gly Leu Leu Thr Glu Ala Asp Val Gln Gln Trp Leu
        450                 455                 460 act tgg tgt aat gca caa agc tgg agc cac tat gaa aac tgg gca ata        1440
Thr Trp Cys Asn Ala Gln Ser Trp Ser His Tyr Glu Asn Trp Ala Ile
465                 470                 475                 480 aac tac aca ttt gat ttc cct gga ata aat gca gat gcc ctc cac cca        1488
Asn Tyr Thr Phe Asp Phe Pro Gly Ile Asn Ala Asp Ala Leu His Pro
                485                 490                 495 gat ctc caa acc acc ccc att gtc cca gac acc agt atc agc agc agt        1536
Asp Leu Gln Thr Thr Pro Ile Val Pro Asp Thr Ser Ile Ser Ser Ser
                500                 505                 510 ggt ggt gaa agc tct gaa gaa ctc agt gaa agc agc ttt ttc aac ctc        1584
Gly Gly Glu Ser Ser Glu Glu Leu Ser Glu Ser Ser Phe Phe Asn Leu
            515                 520                 525 atc act cca ggc gcc tgg aac agt gaa acc ccg cgc tct agt acg ccc        1632
Ile Thr Pro Gly Ala Trp Asn Ser Glu Thr Pro Arg Ser Ser Thr Pro
        530                 535                 540 gtc ccc ggg acc agt tca gga gaa tca ttt gtc gga agc cca gtt tcc        1680
Val Pro Gly Thr Ser Ser Gly Glu Ser Phe Val Gly Ser Pro Val Ser
545                 550                 555                 560 tcc gaa gtg gta gcc gcg tcg tgg gag gaa gct ttt tac acg ccg ctt        1728
Ser Glu Val Val Ala Ala Ser Trp Glu Glu Ala Phe Tyr Thr Pro Leu
                565                 570                 575 gcc gat cag ttt cgt gaa ctg tta gta ggg gtt gac ttt gta tgg gat        1776
Ala Asp Gln Phe Arg Glu Leu Leu Val Gly Val Asp Phe Val Trp Asp
                580                 585                 590 ggt gtg agg gga ttg cct gtt tgc tgt gtg gaa cat ata aac aac agt        1824
Gly Val Arg Gly Leu Pro Val Cys Cys Val Glu His Ile Asn Asn Ser
            595                 600                 605 ggg gga ggg ttg ggg ctt tgc cct cat tgt att aat gtg gga gct tgg        1872
Gly Gly Gly Leu Gly Leu Cys Pro His Cys Ile Asn Val Gly Ala Trp
        610                 615                 620 tat aat gga tgg aaa ttt aga gag ttt act cca gac tta gtg cgc tgc        1920
Tyr Asn Gly Trp Lys Phe Arg Glu Phe Thr Pro Asp Leu Val Arg Cys
625                 630                 635                 640 agt tgt cat gta gga gcc tct aac cca ttt tct gtg tta act tgt aaa        1968
```

```
                  Ser Cys His Val Gly Ala Ser Asn Pro Phe Ser Val Leu Thr Cys Lys
                                  645                 650                 655 aaa tgt gct tac ctg tct gga tta caa agt ttt gta gat tat gag                          2013
Lys Cys Ala Tyr Leu Ser Gly Leu Gln Ser Phe Val Asp Tyr Glu
                660                 665                 670
```

<210> SEQ ID NO 82
<211> LENGTH: 671
<212> TYPE: PRT
<213> ORGANISM: erythrovirus

<400> SEQUENCE: 82

```
Met Glu Leu Phe Arg Gly Val Leu His Ile Ser Ser Asn Ile Leu Asp
 1               5                  10                  15

Cys Ala Asn Asp Asn Trp Trp Cys Ser Met Leu Asp Leu Asp Thr Ser
                20                  25                  30

Asp Trp Glu Pro Leu Thr His Ser Asn Arg Leu Met Ala Ile Tyr Leu
            35                  40                  45

Ser Ser Val Ala Ser Lys Leu Asp Phe Thr Gly Gly Pro Leu Ala Gly
        50                  55                  60

Cys Leu Tyr Phe Phe Gln Val Glu Cys Asn Lys Phe Glu Glu Gly Tyr
 65              70                  75                  80

His Ile His Val Val Ile Gly Gly Pro Gly Leu Asn Ala Arg Asn Leu
                85                  90                  95

Thr Val Cys Val Glu Gly Leu Phe Asn Asn Val Leu Tyr His Leu Val
                100                 105                 110

Thr Glu Ser Val Lys Leu Lys Phe Leu Pro Gly Met Thr Thr Lys Gly
            115                 120                 125

Lys Tyr Phe Arg Asp Gly Glu Gln Phe Ile Glu Asn Tyr Leu Met Lys
        130                 135                 140

Lys Ile Pro Leu Asn Val Val Trp Cys Val Thr Asn Ile Asp Gly Tyr
145                 150                 155                 160

Ile Asp Thr Cys Ile Ser Ala Ser Phe Arg Arg Gly Ala Cys His Ala
                165                 170                 175

Lys Arg Pro Arg Ile Thr Ala Asn Thr Asp Ser Ala Thr Asn Glu Thr
                180                 185                 190

Gly Glu Ser Ser Cys Gly Gly Gly Asp Val Val Pro Phe Ala Gly Lys
            195                 200                 205

Gly Thr Lys Ala Gly Leu Lys Phe Gln Thr Met Val Asn Trp Leu Cys
        210                 215                 220

Glu Asn Arg Val Phe Thr Glu Asp Lys Trp Lys Leu Val Asp Phe Asn
225                 230                 235                 240

Gln Tyr Thr Leu Leu Ser Ser Ser His Ser Gly Ser Phe Gln Ile Gln
                245                 250                 255

Ser Ala Leu Lys Leu Ala Ile Tyr Lys Ala Thr Asn Leu Val Pro Thr
                260                 265                 270

Ser Thr Phe Leu Leu His Ser Asp Phe Glu Gln Val Thr Cys Ile Lys
            275                 280                 285

Glu Asn Lys Ile Val Lys Leu Leu Leu Cys Gln Asn Tyr Asp Pro Leu
        290                 295                 300

Leu Val Gly Gln His Val Leu Arg Trp Ile Asp Lys Lys Cys Gly Lys
305                 310                 315                 320

Lys Asn Thr Leu Trp Phe Tyr Gly Pro Pro Ser Thr Gly Lys Thr Asn
                325                 330                 335

Leu Ala Met Ala Ile Ala Lys Thr Val Pro Val Tyr Gly Met Val Asn
                340                 345                 350
```

```
Trp Asn Asn Glu Asn Phe Pro Phe Asn Asp Val Ala Gly Lys Ser Leu
        355                 360                 365

Val Val Trp Asp Glu Gly Ile Ile Lys Ser Thr Ile Val Glu Ala Ala
370                 375                 380

Lys Ala Ile Leu Gly Gly Gln Pro Thr Arg Val Asp Gln Lys Met Arg
385                 390                 395                 400

Gly Ser Val Ala Val Pro Gly Val Pro Val Val Ile Thr Ser Asn Gly
                405                 410                 415

Asp Ile Thr Phe Val Val Ser Gly Asn Thr Thr Thr Val His Ala
                420                 425                 430

Lys Ala Leu Lys Glu Arg Met Val Lys Leu Asn Phe Thr Ile Arg Cys
        435                 440                 445

Ser Pro Asp Met Gly Leu Leu Thr Glu Ala Asp Val Gln Gln Trp Leu
        450                 455                 460

Thr Trp Cys Asn Ala Gln Ser Trp Ser His Tyr Glu Asn Trp Ala Ile
465                 470                 475                 480

Asn Tyr Thr Phe Asp Phe Pro Gly Ile Asn Ala Asp Ala Leu His Pro
                485                 490                 495

Asp Leu Gln Thr Thr Pro Ile Val Pro Asp Thr Ser Ile Ser Ser Ser
                500                 505                 510

Gly Gly Glu Ser Ser Glu Glu Leu Ser Glu Ser Ser Phe Phe Asn Leu
        515                 520                 525

Ile Thr Pro Gly Ala Trp Asn Ser Glu Thr Pro Arg Ser Ser Thr Pro
        530                 535                 540

Val Pro Gly Thr Ser Ser Gly Glu Ser Phe Val Gly Ser Pro Val Ser
545                 550                 555                 560

Ser Glu Val Val Ala Ala Ser Trp Glu Glu Ala Phe Tyr Thr Pro Leu
                565                 570                 575

Ala Asp Gln Phe Arg Glu Leu Leu Val Gly Val Asp Phe Val Trp Asp
                580                 585                 590

Gly Val Arg Gly Leu Pro Val Cys Cys Val Glu His Ile Asn Asn Ser
        595                 600                 605

Gly Gly Gly Leu Gly Leu Cys Pro His Cys Ile Asn Val Gly Ala Trp
        610                 615                 620

Tyr Asn Gly Trp Lys Phe Arg Glu Phe Thr Pro Asp Leu Val Arg Cys
625                 630                 635                 640

Ser Cys His Val Gly Ala Ser Asn Pro Phe Ser Val Leu Thr Cys Lys
                645                 650                 655

Lys Cys Ala Tyr Leu Ser Gly Leu Gln Ser Phe Val Asp Tyr Glu
                660                 665                 670
```

<210> SEQ ID NO 83
<211> LENGTH: 222
<212> TYPE: DNA
<213> ORGANISM: erythroviurs
<220> FEATURE:
<221> NAME/KEY: CDS
<222> LOCATION: (1)..(222)
<223> OTHER INFORMATION: Encodes amino acids 672-745 of SEQ ID NO: 2.

<400> SEQUENCE: 83

```
atg cag atg ccc tcc acc cag atc tcc aaa cca ccc cca ttg tcc cag    48
Met Gln Met Pro Ser Thr Gln Ile Ser Lys Pro Pro Pro Leu Ser Gln
1               5                   10                  15 aca cca gta tca gca gca gtg gtg gtg aaa gct ctg aag aac tca gtg    96
Thr Pro Val Ser Ala Ala Val Val Val Lys Ala Leu Lys Asn Ser Val
            20                  25                  30
```

```
aaa gca gct ttt tca acc tca tca ctc cag gcg cct gga aca gtg aaa        144
Lys Ala Ala Phe Ser Thr Ser Ser Leu Gln Ala Pro Gly Thr Val Lys
         35                  40                  45 ccc cgc gct cta gta cgc ccg tcc ccg gga cca gtt cag gag aat cat        192
Pro Arg Ala Leu Val Arg Pro Ser Pro Gly Pro Val Gln Glu Asn His
 50                  55                  60 ttg tcg gaa gcc cag ttt cct ccg aag tgg                                222
Leu Ser Glu Ala Gln Phe Pro Pro Lys Trp
 65                  70

<210> SEQ ID NO 84
<211> LENGTH: 74
<212> TYPE: PRT
<213> ORGANISM: erythroviurs

<400> SEQUENCE: 84

Met Gln Met Pro Ser Thr Gln Ile Ser Lys Pro Pro Leu Ser Gln
 1               5                  10                  15

Thr Pro Val Ser Ala Ala Val Val Lys Ala Leu Lys Asn Ser Val
                 20                  25                  30

Lys Ala Ala Phe Ser Thr Ser Ser Leu Gln Ala Pro Gly Thr Val Lys
         35                  40                  45

Pro Arg Ala Leu Val Arg Pro Ser Pro Gly Pro Val Gln Glu Asn His
 50                  55                  60

Leu Ser Glu Ala Gln Phe Pro Pro Lys Trp
 65                  70

<210> SEQ ID NO 85
<211> LENGTH: 2343
<212> TYPE: DNA
<213> ORGANISM: erythrovirus
<220> FEATURE:
<221> NAME/KEY: CDS
<222> LOCATION: (1)..(2343)
<223> OTHER INFORMATION: Encodes amino acids 75-855 of SEQ ID NO: 2.

<400> SEQUENCE: 85 atg agt aaa acc act aac aaa tgg tgg gaa agc agt gac aaa ttt gcc        48
Met Ser Lys Thr Thr Asn Lys Trp Trp Glu Ser Ser Asp Lys Phe Ala
 1               5                  10                  15 cag gac gtg tat aag cag ttt gtg caa ttt tat gaa aaa gct act gga        96
Gln Asp Val Tyr Lys Gln Phe Val Gln Phe Tyr Glu Lys Ala Thr Gly
                 20                  25                  30 aca gac tta gag ctt att caa att tta aaa gac cat tac aac att tct        144
Thr Asp Leu Glu Leu Ile Gln Ile Leu Lys Asp His Tyr Asn Ile Ser
         35                  40                  45 tta gat aat cct tta gaa aac ccc tct tct tta ttt gac tta gtt gct        192
Leu Asp Asn Pro Leu Glu Asn Pro Ser Ser Leu Phe Asp Leu Val Ala
 50                  55                  60 cgc att aaa agt aat ctt aaa aac tct cca gac cta tat agt cat cat        240
Arg Ile Lys Ser Asn Leu Lys Asn Ser Pro Asp Leu Tyr Ser His His
 65                  70                  75                  80 ttt cag agc cat gga cag tta tct gac cac ccc cat gcc tta tca tcc        288
Phe Gln Ser His Gly Gln Leu Ser Asp His Pro His Ala Leu Ser Ser
                 85                  90                  95 agt aac agt agt gca gaa cct aga gga gaa aat gca gta tta tct agt        336
Ser Asn Ser Ser Ala Glu Pro Arg Gly Glu Asn Ala Val Leu Ser Ser
                100                 105                 110 gaa gac tta cac aag cct ggg caa gtt agc ata caa tta ccc ggt act        384
Glu Asp Leu His Lys Pro Gly Gln Val Ser Ile Gln Leu Pro Gly Thr
                115                 120                 125
```

```
aac tat gtt ggg cct ggc aat gag cta caa gct ggg cct ccg cag aat       432
Asn Tyr Val Gly Pro Gly Asn Glu Leu Gln Ala Gly Pro Pro Gln Asn
    130                 135                 140 gct gtg gac agt gct gca agg att cat gac ttt agg tat agc caa ttg       480
Ala Val Asp Ser Ala Ala Arg Ile His Asp Phe Arg Tyr Ser Gln Leu
145                 150                 155                 160 gct aag ttg gga ata aat cct tat aca cat tgg acg gta gca gat gaa       528
Ala Lys Leu Gly Ile Asn Pro Tyr Thr His Trp Thr Val Ala Asp Glu
                165                 170                 175 gaa ttg tta aaa aat ata aaa aat gaa aca ggg ttt caa gca caa gca       576
Glu Leu Leu Lys Asn Ile Lys Asn Glu Thr Gly Phe Gln Ala Gln Ala
            180                 185                 190 gta aaa gat tac ttt act tta aaa ggt gca gct gcc cct gtg gcc cat       624
Val Lys Asp Tyr Phe Thr Leu Lys Gly Ala Ala Ala Pro Val Ala His
        195                 200                 205 ttt caa gga agt tta ccg gaa gtg ccc gcg tac aac gcc tca gaa aaa       672
Phe Gln Gly Ser Leu Pro Glu Val Pro Ala Tyr Asn Ala Ser Glu Lys
    210                 215                 220 tac ccc agc atg act tca gtt aac tct gca gaa gcc agc act ggt gca       720
Tyr Pro Ser Met Thr Ser Val Asn Ser Ala Glu Ala Ser Thr Gly Ala
225                 230                 235                 240 ggc ggg gga ggt agc aac cct aca aaa agc atg tgg agt gaa ggg gct       768
Gly Gly Gly Gly Ser Asn Pro Thr Lys Ser Met Trp Ser Glu Gly Ala
                245                 250                 255 aca ttt act gct aat tct gta acg tgt aca ttc tct agg caa ttt tta       816
Thr Phe Thr Ala Asn Ser Val Thr Cys Thr Phe Ser Arg Gln Phe Leu
            260                 265                 270 att cca tat gat cca gag cat cat tat aaa gtg ttc tct cca gca gct       864
Ile Pro Tyr Asp Pro Glu His His Tyr Lys Val Phe Ser Pro Ala Ala
        275                 280                 285 agt agc tgc cac aat gct agt ggg aaa gag gca aaa gtg tgc act att       912
Ser Ser Cys His Asn Ala Ser Gly Lys Glu Ala Lys Val Cys Thr Ile
    290                 295                 300 agt ccc att atg ggg tac tct act ccg tgg aga tac tta gat ttt aat       960
Ser Pro Ile Met Gly Tyr Ser Thr Pro Trp Arg Tyr Leu Asp Phe Asn
305                 310                 315                 320 gct tta aat ttg ttt ttc tca cca tta gag ttt cag cac tta att gaa      1008
Ala Leu Asn Leu Phe Phe Ser Pro Leu Glu Phe Gln His Leu Ile Glu
                325                 330                 335 aat tat ggt agt ata gct cca gat gct tta act gta act att tca gaa      1056
Asn Tyr Gly Ser Ile Ala Pro Asp Ala Leu Thr Val Thr Ile Ser Glu
            340                 345                 350 att gct gta aaa gat gtc aca gac aaa aca gga gga ggt gtg caa gtt      1104
Ile Ala Val Lys Asp Val Thr Asp Lys Thr Gly Gly Gly Val Gln Val
        355                 360                 365 act gac agc acc aca gga cgt ttg tgt atg tta gtg gat cat gag tat      1152
Thr Asp Ser Thr Thr Gly Arg Leu Cys Met Leu Val Asp His Glu Tyr
    370                 375                 380 aaa tac cca tat gtg cta ggt cag gga caa gac aca cta gct cca gaa      1200
Lys Tyr Pro Tyr Val Leu Gly Gln Gly Gln Asp Thr Leu Ala Pro Glu
385                 390                 395                 400 ctg ccc att tgg gtt tac ttt ccc ccc cag tat gct tac tta aca gta      1248
Leu Pro Ile Trp Val Tyr Phe Pro Pro Gln Tyr Ala Tyr Leu Thr Val
                405                 410                 415 ggt gaa gta aac aca caa gga att tca gga gac agc aaa aaa ttg gct      1296
Gly Glu Val Asn Thr Gln Gly Ile Ser Gly Asp Ser Lys Lys Leu Ala
            420                 425                 430 agt gaa gaa tca gct ttt tat gtg tta gag cac agt tca ttt gaa ctt      1344
Ser Glu Glu Ser Ala Phe Tyr Val Leu Glu His Ser Ser Phe Glu Leu
        435                 440                 445
```

```
ttg ggt aca ggg gga tct gcc act atg tcc tac aaa ttt cca gct gtg    1392
Leu Gly Thr Gly Gly Ser Ala Thr Met Ser Tyr Lys Phe Pro Ala Val
    450             455             460 ccc cca gaa aac cta gaa ggc tgc agc caa cat ttt tat gaa atg tac    1440
Pro Pro Glu Asn Leu Glu Gly Cys Ser Gln His Phe Tyr Glu Met Tyr
465             470             475             480 aac cct ttg tac ggt tct cgt tta ggg gta cct gac aca tta gga ggg    1488
Asn Pro Leu Tyr Gly Ser Arg Leu Gly Val Pro Asp Thr Leu Gly Gly
                485             490             495 gac cct aaa ttt aga tca ttg aca cac gaa gac cac gca att cag cca    1536
Asp Pro Lys Phe Arg Ser Leu Thr His Glu Asp His Ala Ile Gln Pro
            500             505             510 caa aac ttt atg cct ggg cca cta ata aat tca gtg tct acc aaa gaa    1584
Gln Asn Phe Met Pro Gly Pro Leu Ile Asn Ser Val Ser Thr Lys Glu
        515             520             525 gga gac aat tct aat aca ggt gct gga aaa gcc ctt acg ggg ctt agt    1632
Gly Asp Asn Ser Asn Thr Gly Ala Gly Lys Ala Leu Thr Gly Leu Ser
    530             535             540 act ggc act agc caa aac acc aga att tcc cta cgc ccc ggg cca gta    1680
Thr Gly Thr Ser Gln Asn Thr Arg Ile Ser Leu Arg Pro Gly Pro Val
545             550             555             560 tct cag cca tac cat cac tgg gac act gat aaa tat gtt aca gga ata    1728
Ser Gln Pro Tyr His His Trp Asp Thr Asp Lys Tyr Val Thr Gly Ile
                565             570             575 aat gcc att tca cat gga caa acc act tat gga aat gct gag gac aaa    1776
Asn Ala Ile Ser His Gly Gln Thr Thr Tyr Gly Asn Ala Glu Asp Lys
            580             585             590 gag tat cag caa ggg gta gga aga ttt cca aat gaa aaa gaa cag ctt    1824
Glu Tyr Gln Gln Gly Val Gly Arg Phe Pro Asn Glu Lys Glu Gln Leu
        595             600             605 aag cag tta caa ggt ctt aac atg cac aca tac ttc cct aat aaa gga    1872
Lys Gln Leu Gln Gly Leu Asn Met His Thr Tyr Phe Pro Asn Lys Gly
    610             615             620 acc caa caa tac aca gac caa att gaa cgc cct ctt atg gtg ggc tct    1920
Thr Gln Gln Tyr Thr Asp Gln Ile Glu Arg Pro Leu Met Val Gly Ser
625             630             635             640 gtt tgg aac aga aga gct ctt cac tat gaa agt cag ctg tgg agt aaa    1968
Val Trp Asn Arg Arg Ala Leu His Tyr Glu Ser Gln Leu Trp Ser Lys
                645             650             655 atc cct aac tta gat gac agt ttt aaa act caa ttt gca gcc cta ggc    2016
Ile Pro Asn Leu Asp Asp Ser Phe Lys Thr Gln Phe Ala Ala Leu Gly
            660             665             670 ggg tgg ggt ttg cat caa cca ccc cct caa ata ttt tta aaa ata cta    2064
Gly Trp Gly Leu His Gln Pro Pro Pro Gln Ile Phe Leu Lys Ile Leu
        675             680             685 cca caa agt ggg cca att gga ggt att aaa tcc atg gga att act act    2112
Pro Gln Ser Gly Pro Ile Gly Gly Ile Lys Ser Met Gly Ile Thr Thr
    690             695             700 tta gtt caa tat gct gtg gga ata atg aca gtt acc atg acc ttt aaa    2160
Leu Val Gln Tyr Ala Val Gly Ile Met Thr Val Thr Met Thr Phe Lys
705             710             715             720 ttg gga cct cga aag gct act gga agg tgg aat ccc agg cct ggc gtt    2208
Leu Gly Pro Arg Lys Ala Thr Gly Arg Trp Asn Pro Gln Pro Gly Val
                725             730             735 tat cct cct cat gca gct ggt cat tta cca tat gta ctg tat gac ccc    2256
Tyr Pro Pro His Ala Ala Gly His Leu Pro Tyr Val Leu Tyr Asp Pro
            740             745             750 aca gct aca gat gca aag caa cac cac aga cac gga tat gaa aag cct    2304
Thr Ala Thr Asp Ala Lys Gln His His Arg His Gly Tyr Glu Lys Pro
        755             760             765
```

```
gaa gaa ttg tgg act gcc aaa agc cgt gtg cac cca ttg                    2343
Glu Glu Leu Trp Thr Ala Lys Ser Arg Val His Pro Leu
    770             775             780
```

<210> SEQ ID NO 86
<211> LENGTH: 781
<212> TYPE: PRT
<213> ORGANISM: erythrovirus

<400> SEQUENCE: 86

```
Met Ser Lys Thr Thr Asn Lys Trp Trp Glu Ser Ser Asp Lys Phe Ala
1               5                   10                  15

Gln Asp Val Tyr Lys Gln Phe Val Gln Phe Tyr Glu Lys Ala Thr Gly
                20                  25                  30

Thr Asp Leu Glu Leu Ile Gln Ile Leu Lys Asp His Tyr Asn Ile Ser
            35                  40                  45

Leu Asp Asn Pro Leu Glu Asn Pro Ser Ser Leu Phe Asp Leu Val Ala
        50                  55                  60

Arg Ile Lys Ser Asn Leu Lys Asn Ser Pro Asp Leu Tyr Ser His His
65                  70                  75                  80

Phe Gln Ser His Gly Gln Leu Ser Asp His Pro His Ala Leu Ser Ser
                85                  90                  95

Ser Asn Ser Ser Ala Glu Pro Arg Gly Glu Asn Ala Val Leu Ser Ser
                100                 105                 110

Glu Asp Leu His Lys Pro Gly Gln Val Ser Ile Gln Leu Pro Gly Thr
            115                 120                 125

Asn Tyr Val Gly Pro Gly Asn Glu Leu Gln Ala Gly Pro Pro Gln Asn
        130                 135                 140

Ala Val Asp Ser Ala Ala Arg Ile His Asp Phe Arg Tyr Ser Gln Leu
145                 150                 155                 160

Ala Lys Leu Gly Ile Asn Pro Tyr Thr His Trp Thr Val Ala Asp Glu
                165                 170                 175

Glu Leu Leu Lys Asn Ile Lys Asn Glu Thr Gly Phe Gln Ala Gln Ala
            180                 185                 190

Val Lys Asp Tyr Phe Thr Leu Lys Gly Ala Ala Ala Pro Val Ala His
        195                 200                 205

Phe Gln Gly Ser Leu Pro Glu Val Pro Ala Tyr Asn Ala Ser Glu Lys
    210                 215                 220

Tyr Pro Ser Met Thr Ser Val Asn Ser Ala Glu Ala Ser Thr Gly Ala
225                 230                 235                 240

Gly Gly Gly Gly Ser Asn Pro Thr Lys Ser Met Trp Ser Glu Gly Ala
                245                 250                 255

Thr Phe Thr Ala Asn Ser Val Thr Cys Thr Phe Ser Arg Gln Phe Leu
            260                 265                 270

Ile Pro Tyr Asp Pro Glu His His Tyr Lys Val Phe Ser Pro Ala Ala
        275                 280                 285

Ser Ser Cys His Asn Ala Ser Gly Lys Glu Ala Lys Val Cys Thr Ile
    290                 295                 300

Ser Pro Ile Met Gly Tyr Ser Thr Pro Trp Arg Tyr Leu Asp Phe Asn
305                 310                 315                 320

Ala Leu Asn Leu Phe Phe Ser Pro Leu Glu Phe Gln His Leu Ile Glu
                325                 330                 335

Asn Tyr Gly Ser Ile Ala Pro Asp Ala Leu Thr Val Thr Ile Ser Glu
            340                 345                 350

Ile Ala Val Lys Asp Val Thr Asp Lys Thr Gly Gly Gly Val Gln Val
        355                 360                 365
```

```
Thr Asp Ser Thr Thr Gly Arg Leu Cys Met Leu Val Asp His Glu Tyr
    370                 375                 380

Lys Tyr Pro Tyr Val Leu Gly Gln Gly Gln Asp Thr Leu Ala Pro Glu
385                 390                 395                 400

Leu Pro Ile Trp Val Tyr Phe Pro Pro Gln Tyr Ala Tyr Leu Thr Val
                405                 410                 415

Gly Glu Val Asn Thr Gln Gly Ile Ser Gly Asp Ser Lys Lys Leu Ala
            420                 425                 430

Ser Glu Glu Ser Ala Phe Tyr Val Leu Glu His Ser Ser Phe Glu Leu
        435                 440                 445

Leu Gly Thr Gly Gly Ser Ala Thr Met Ser Tyr Lys Phe Pro Ala Val
    450                 455                 460

Pro Pro Glu Asn Leu Glu Gly Cys Ser Gln His Phe Tyr Glu Met Tyr
465                 470                 475                 480

Asn Pro Leu Tyr Gly Ser Arg Leu Gly Val Pro Asp Thr Leu Gly Gly
                485                 490                 495

Asp Pro Lys Phe Arg Ser Leu Thr His Glu Asp His Ala Ile Gln Pro
            500                 505                 510

Gln Asn Phe Met Pro Gly Pro Leu Ile Asn Ser Val Ser Thr Lys Glu
        515                 520                 525

Gly Asp Asn Ser Asn Thr Gly Ala Gly Lys Ala Leu Thr Gly Leu Ser
    530                 535                 540

Thr Gly Thr Ser Gln Asn Thr Arg Ile Ser Leu Arg Pro Gly Pro Val
545                 550                 555                 560

Ser Gln Pro Tyr His His Trp Asp Thr Asp Lys Tyr Val Thr Gly Ile
                565                 570                 575

Asn Ala Ile Ser His Gly Gln Thr Thr Tyr Gly Asn Ala Glu Asp Lys
            580                 585                 590

Glu Tyr Gln Gln Gly Val Gly Arg Phe Pro Asn Glu Lys Glu Gln Leu
        595                 600                 605

Lys Gln Leu Gln Gly Leu Asn Met His Thr Tyr Phe Pro Asn Lys Gly
    610                 615                 620

Thr Gln Gln Tyr Thr Asp Gln Ile Glu Arg Pro Leu Met Val Gly Ser
625                 630                 635                 640

Val Trp Asn Arg Arg Ala Leu His Tyr Glu Ser Gln Leu Trp Ser Lys
                645                 650                 655

Ile Pro Asn Leu Asp Asp Ser Phe Lys Thr Gln Phe Ala Ala Leu Gly
            660                 665                 670

Gly Trp Gly Leu His Gln Pro Pro Gln Ile Phe Leu Lys Ile Leu
        675                 680                 685

Pro Gln Ser Gly Pro Ile Gly Gly Ile Lys Ser Met Gly Ile Thr Thr
    690                 695                 700

Leu Val Gln Tyr Ala Val Gly Ile Met Thr Val Thr Met Thr Phe Lys
705                 710                 715                 720

Leu Gly Pro Arg Lys Ala Thr Gly Arg Trp Asn Pro Gln Pro Gly Val
                725                 730                 735

Tyr Pro Pro His Ala Ala Gly His Leu Pro Tyr Val Leu Tyr Asp Pro
            740                 745                 750

Thr Ala Thr Asp Ala Lys Gln His His Arg His Gly Tyr Glu Lys Pro
        755                 760                 765

Glu Glu Leu Trp Thr Ala Lys Ser Arg Val His Pro Leu
    770                 775                 780
```

<210> SEQ ID NO 87
<211> LENGTH: 681
<212> TYPE: DNA
<213> ORGANISM: erythrovirus
<220> FEATURE:
<221> NAME/KEY: CDS
<222> LOCATION: (1)..(681)
<223> OTHER INFORMATION: Encodes amino acids 782-1008 of SEQ ID NO: 2.

<400> SEQUENCE: 87

```
atg agt aaa acc act aac aaa tgg tgg gaa agc agt gac aaa ttt gcc        48
Met Ser Lys Thr Thr Asn Lys Trp Trp Glu Ser Ser Asp Lys Phe Ala
1               5                   10                  15 cag gac gtg tat aag cag ttt gtg caa ttt tat gaa aaa gct act gga        96
Gln Asp Val Tyr Lys Gln Phe Val Gln Phe Tyr Glu Lys Ala Thr Gly
            20                  25                  30 aca gac tta gag ctt att caa att tta aaa gac cat tac aac att tct       144
Thr Asp Leu Glu Leu Ile Gln Ile Leu Lys Asp His Tyr Asn Ile Ser
        35                  40                  45 tta gat aat cct tta gaa aac ccc tct tct tta ttt gac tta gtt gct       192
Leu Asp Asn Pro Leu Glu Asn Pro Ser Ser Leu Phe Asp Leu Val Ala
50                  55                  60 cgc att aaa agt aat ctt aaa aac tct cca gac cta tat agt cat cat       240
Arg Ile Lys Ser Asn Leu Lys Asn Ser Pro Asp Leu Tyr Ser His His
65                  70                  75                  80 ttt cag agc cat gga cag tta tct gac cac ccc cat gcc tta tca tcc       288
Phe Gln Ser His Gly Gln Leu Ser Asp His Pro His Ala Leu Ser Ser
                85                  90                  95 agt aac agt agt gca gaa cct aga gga gaa aat gca gta tta tct agt       336
Ser Asn Ser Ser Ala Glu Pro Arg Gly Glu Asn Ala Val Leu Ser Ser
            100                 105                 110 gaa gac tta cac aag cct ggg caa gtt agc ata caa tta ccc ggt act       384
Glu Asp Leu His Lys Pro Gly Gln Val Ser Ile Gln Leu Pro Gly Thr
        115                 120                 125 aac tat gtt ggg cct ggc aat gag cta caa gct ggg cct ccg cag aat       432
Asn Tyr Val Gly Pro Gly Asn Glu Leu Gln Ala Gly Pro Pro Gln Asn
    130                 135                 140 gct gtg gac agt gct gca agg att cat gac ttt agg tat agc caa ttg       480
Ala Val Asp Ser Ala Ala Arg Ile His Asp Phe Arg Tyr Ser Gln Leu
145                 150                 155                 160 gct aag ttg gga ata aat cct tat aca cat tgg acg gta gca gat gaa       528
Ala Lys Leu Gly Ile Asn Pro Tyr Thr His Trp Thr Val Ala Asp Glu
                165                 170                 175 gaa ttg tta aaa aat ata aaa aat gaa aca ggg ttt caa gca caa gca       576
Glu Leu Leu Lys Asn Ile Lys Asn Glu Thr Gly Phe Gln Ala Gln Ala
            180                 185                 190 gta aaa gat tac ttt act tta aaa ggt gca gct gcc cct gtg gcc cat       624
Val Lys Asp Tyr Phe Thr Leu Lys Gly Ala Ala Ala Pro Val Ala His
        195                 200                 205 ttt caa gga agt tta ccg gaa gtg ccc gcg tac aac gcc tca gaa aaa       672
Phe Gln Gly Ser Leu Pro Glu Val Pro Ala Tyr Asn Ala Ser Glu Lys
    210                 215                 220 tac ccc agc                                                           681
Tyr Pro Ser
225
```

<210> SEQ ID NO 88
<211> LENGTH: 227
<212> TYPE: PRT
<213> ORGANISM: erythrovirus

<400> SEQUENCE: 88

Met Ser Lys Thr Thr Asn Lys Trp Trp Glu Ser Ser Asp Lys Phe Ala

```
                1               5                   10                  15
Gln Asp Val Tyr Lys Gln Phe Val Gln Phe Tyr Glu Lys Ala Thr Gly
                    20                  25                  30

Thr Asp Leu Glu Leu Ile Gln Ile Leu Lys Asp His Tyr Asn Ile Ser
            35                  40                      45

Leu Asp Asn Pro Leu Glu Asn Pro Ser Ser Leu Phe Asp Leu Val Ala
        50                  55                  60

Arg Ile Lys Ser Asn Leu Lys Asn Ser Pro Asp Leu Tyr Ser His His
65                      70                  75                  80

Phe Gln Ser His Gly Gln Leu Ser Asp His Pro His Ala Leu Ser Ser
                    85                  90                  95

Ser Asn Ser Ser Ala Glu Pro Arg Gly Glu Asn Ala Val Leu Ser Ser
                100                 105                 110

Glu Asp Leu His Lys Pro Gly Gln Val Ser Ile Gln Leu Pro Gly Thr
            115                 120                 125

Asn Tyr Val Gly Pro Gly Asn Glu Leu Gln Ala Gly Pro Pro Gln Asn
        130                 135                 140

Ala Val Asp Ser Ala Ala Arg Ile His Asp Phe Arg Tyr Ser Gln Leu
145                 150                 155                 160

Ala Lys Leu Gly Ile Asn Pro Tyr Thr His Trp Thr Val Ala Asp Glu
                165                 170                 175

Glu Leu Leu Lys Asn Ile Lys Asn Glu Thr Gly Phe Gln Ala Gln Ala
                180                 185                 190

Val Lys Asp Tyr Phe Thr Leu Lys Gly Ala Ala Pro Val Ala His
            195                 200                 205

Phe Gln Gly Ser Leu Pro Glu Val Pro Ala Tyr Asn Ala Ser Glu Lys
        210                 215                 220

Tyr Pro Ser
225
```

<210> SEQ ID NO 89
<211> LENGTH: 306
<212> TYPE: DNA
<213> ORGANISM: erythrovirus
<220> FEATURE:
<221> NAME/KEY: CDS
<222> LOCATION: (1)..(306)
<223> OTHER INFORMATION: Encodes amino acids 228-329 of SEQ ID NO: 2.

<400> SEQUENCE: 89

```
ttg ctc gca tta aaa gta atc tta aaa act ctc cag acc tat ata gtc    48
Leu Leu Ala Leu Lys Val Ile Leu Lys Thr Leu Gln Thr Tyr Ile Val
1               5                   10                  15 atc att ttc aga gcc atg gac agt tat ctg acc acc ccc atg cct tat    96
Ile Ile Phe Arg Ala Met Asp Ser Tyr Leu Thr Thr Pro Met Pro Tyr
            20                  25                  30 cat cca gta aca gta gtg cag aac cta gag gag aaa atg cag tat tat   144
His Pro Val Thr Val Val Gln Asn Leu Glu Glu Lys Met Gln Tyr Tyr
        35                  40                  45 cta gtg aag act tac aca agc ctg ggc aag tta gca tac aat tac ccg   192
Leu Val Lys Thr Tyr Thr Ser Leu Gly Lys Leu Ala Tyr Asn Tyr Pro
    50                  55                  60 gta cta act atg ttg ggc ctg gca atg agc tac aag ctg ggc ctc cgc   240
Val Leu Thr Met Leu Gly Leu Ala Met Ser Tyr Lys Leu Gly Leu Arg
65                  70                  75                  80 aga atg ctg tgg aca gtg ctg caa gga ttc atg act tta ggt ata gcc   288
Arg Met Leu Trp Thr Val Leu Gln Gly Phe Met Thr Leu Gly Ile Ala
                85                  90                  95
```

```
aat tgg cta agt tgg gaa                                              306
Asn Trp Leu Ser Trp Glu
            100

<210> SEQ ID NO 90
<211> LENGTH: 102
<212> TYPE: PRT
<213> ORGANISM: erythrovirus

<400> SEQUENCE: 90

Leu Leu Ala Leu Lys Val Ile Leu Lys Thr Leu Gln Thr Tyr Ile Val
1               5                   10                  15

Ile Ile Phe Arg Ala Met Asp Ser Tyr Leu Thr Thr Pro Met Pro Tyr
            20                  25                  30

His Pro Val Thr Val Val Gln Asn Leu Glu Glu Lys Met Gln Tyr Tyr
        35                  40                  45

Leu Val Lys Thr Tyr Thr Ser Leu Gly Lys Leu Ala Tyr Asn Tyr Pro
    50                  55                  60

Val Leu Thr Met Leu Gly Leu Ala Met Ser Tyr Lys Leu Gly Leu Arg
65                  70                  75                  80

Arg Met Leu Trp Thr Val Leu Gln Gly Phe Met Thr Leu Gly Ile Ala
                85                  90                  95

Asn Trp Leu Ser Trp Glu
            100

<210> SEQ ID NO 91
<211> LENGTH: 1662
<212> TYPE: DNA
<213> ORGANISM: erythrovirus
<220> FEATURE:
<221> NAME/KEY: CDS
<222> LOCATION: (1)..(1662)
<223> OTHER INFORMATION: Encodes amino acids 103-656 of SEQ ID NO: 2.

<400> SEQUENCE: 91 atg act tca gtt aac tct gca gaa gcc agc act ggt gca ggc ggg gga    48
Met Thr Ser Val Asn Ser Ala Glu Ala Ser Thr Gly Ala Gly Gly Gly
1               5                   10                  15 ggt agc aac cct aca aaa agc atg tgg agt gaa ggg gct aca ttt act    96
Gly Ser Asn Pro Thr Lys Ser Met Trp Ser Glu Gly Ala Thr Phe Thr
            20                  25                  30 gct aat tct gta acg tgt aca ttc tct agg caa ttt tta att cca tat   144
Ala Asn Ser Val Thr Cys Thr Phe Ser Arg Gln Phe Leu Ile Pro Tyr
        35                  40                  45 gat cca gag cat cat tat aaa gtg ttc tct cca gca gct agt agc tgc   192
Asp Pro Glu His His Tyr Lys Val Phe Ser Pro Ala Ala Ser Ser Cys
    50                  55                  60 cac aat gct agt ggg aaa gag gca aaa gtg tgc act att agt ccc att   240
His Asn Ala Ser Gly Lys Glu Ala Lys Val Cys Thr Ile Ser Pro Ile
65                  70                  75                  80 atg ggg tac tct act ccg tgg aga tac tta gat ttt aat gct tta aat   288
Met Gly Tyr Ser Thr Pro Trp Arg Tyr Leu Asp Phe Asn Ala Leu Asn
                85                  90                  95 ttg ttt ttc tca cca tta gag ttt cag cac tta att gaa aat tat ggt   336
Leu Phe Phe Ser Pro Leu Glu Phe Gln His Leu Ile Glu Asn Tyr Gly
            100                 105                 110 agt ata gct cca gat gct tta act gta act att tca gaa att gct gta   384
Ser Ile Ala Pro Asp Ala Leu Thr Val Thr Ile Ser Glu Ile Ala Val
        115                 120                 125 aaa gat gtc aca gac aaa aca gga gga ggt gtg caa gtt act gac agc   432
Lys Asp Val Thr Asp Lys Thr Gly Gly Gly Val Gln Val Thr Asp Ser
    130                 135                 140
```

```
acc aca gga cgt ttg tgt atg tta gtg gat cat gag tat aaa tac cca    480
Thr Thr Gly Arg Leu Cys Met Leu Val Asp His Glu Tyr Lys Tyr Pro
145                 150                 155                 160 tat gtg cta ggt cag gga caa gac aca cta gct cca gaa ctg ccc att    528
Tyr Val Leu Gly Gln Gly Gln Asp Thr Leu Ala Pro Glu Leu Pro Ile
                165                 170                 175 tgg gtt tac ttt ccc ccc cag tat gct tac tta aca gta ggt gaa gta    576
Trp Val Tyr Phe Pro Pro Gln Tyr Ala Tyr Leu Thr Val Gly Glu Val
            180                 185                 190 aac aca caa gga att tca gga gac agc aaa aaa ttg gct agt gaa gaa    624
Asn Thr Gln Gly Ile Ser Gly Asp Ser Lys Lys Leu Ala Ser Glu Glu
        195                 200                 205 tca gct ttt tat gtg tta gag cac agt tca ttt gaa ctt ttg ggt aca    672
Ser Ala Phe Tyr Val Leu Glu His Ser Ser Phe Glu Leu Leu Gly Thr
    210                 215                 220 ggg gga tct gcc act atg tcc tac aaa ttt cca gct gtg ccc cca gaa    720
Gly Gly Ser Ala Thr Met Ser Tyr Lys Phe Pro Ala Val Pro Pro Glu
225                 230                 235                 240 aac cta gaa ggc tgc agc caa cat ttt tat gaa atg tac aac cct ttg    768
Asn Leu Glu Gly Cys Ser Gln His Phe Tyr Glu Met Tyr Asn Pro Leu
                245                 250                 255 tac ggt tct cgt tta ggg gta cct gac aca tta gga ggg gac cct aaa    816
Tyr Gly Ser Arg Leu Gly Val Pro Asp Thr Leu Gly Gly Asp Pro Lys
            260                 265                 270 ttt aga tca ttg aca cac gaa gac cac gca att cag cca caa aac ttt    864
Phe Arg Ser Leu Thr His Glu Asp His Ala Ile Gln Pro Gln Asn Phe
        275                 280                 285 atg cct ggg cca cta ata aat tca gtg tct acc aaa gaa gga gac aat    912
Met Pro Gly Pro Leu Ile Asn Ser Val Ser Thr Lys Glu Gly Asp Asn
    290                 295                 300 tct aat aca ggt gct gga aaa gcc ctt acg ggg ctt agt act ggc act    960
Ser Asn Thr Gly Ala Gly Lys Ala Leu Thr Gly Leu Ser Thr Gly Thr
305                 310                 315                 320 agc caa aac acc aga att tcc cta cgc ccc ggg cca gta tct cag cca    1008
Ser Gln Asn Thr Arg Ile Ser Leu Arg Pro Gly Pro Val Ser Gln Pro
                325                 330                 335 tac cat cac tgg gac act gat aaa tat gtt aca gga ata aat gcc att    1056
Tyr His His Trp Asp Thr Asp Lys Tyr Val Thr Gly Ile Asn Ala Ile
            340                 345                 350 tca cat gga caa acc act tat gga aat gct gag gac aaa gag tat cag    1104
Ser His Gly Gln Thr Thr Tyr Gly Asn Ala Glu Asp Lys Glu Tyr Gln
        355                 360                 365 caa ggg gta gga aga ttt cca aat gaa aaa gaa cag ctt aag cag tta    1152
Gln Gly Val Gly Arg Phe Pro Asn Glu Lys Glu Gln Leu Lys Gln Leu
    370                 375                 380 caa ggt ctt aac atg cac aca tac ttc cct aat aaa gga acc caa caa    1200
Gln Gly Leu Asn Met His Thr Tyr Phe Pro Asn Lys Gly Thr Gln Gln
385                 390                 395                 400 tac aca gac caa att gaa cgc cct ctt atg gtg ggc tct gtt tgg aac    1248
Tyr Thr Asp Gln Ile Glu Arg Pro Leu Met Val Gly Ser Val Trp Asn
                405                 410                 415 aga aga gct ctt cac tat gaa agt cag ctg tgg agt aaa atc cct aac    1296
Arg Arg Ala Leu His Tyr Glu Ser Gln Leu Trp Ser Lys Ile Pro Asn
            420                 425                 430 tta gat gac agt ttt aaa act caa ttt gca gcc cta ggc ggg tgg ggt    1344
Leu Asp Asp Ser Phe Lys Thr Gln Phe Ala Ala Leu Gly Gly Trp Gly
        435                 440                 445 ttg cat caa cca ccc cct caa ata ttt tta aaa ata cta cca caa agt    1392
Leu His Gln Pro Pro Pro Gln Ile Phe Leu Lys Ile Leu Pro Gln Ser
    450                 455                 460
```

```
ggg cca att gga ggt att aaa tcc atg gga att act act tta gtt caa    1440
Gly Pro Ile Gly Gly Ile Lys Ser Met Gly Ile Thr Thr Leu Val Gln
465                 470                 475                 480 tat gct gtg gga ata atg aca gtt acc atg acc ttt aaa ttg gga cct    1488
Tyr Ala Val Gly Ile Met Thr Val Thr Met Thr Phe Lys Leu Gly Pro
                485                 490                 495 cga aag gct act gga agg tgg aat ccc cag cct ggc gtt tat cct cct    1536
Arg Lys Ala Thr Gly Arg Trp Asn Pro Gln Pro Gly Val Tyr Pro Pro
            500                 505                 510 cat gca gct ggt cat tta cca tat gta ctg tat gac ccc aca gct aca    1584
His Ala Ala Gly His Leu Pro Tyr Val Leu Tyr Asp Pro Thr Ala Thr
        515                 520                 525 gat gca aag caa cac cac aga cac gga tat gaa aag cct gaa gaa ttg    1632
Asp Ala Lys Gln His His Arg His Gly Tyr Glu Lys Pro Glu Glu Leu
530                 535                 540 tgg act gcc aaa agc cgt gtg cac cca ttg                            1662
Trp Thr Ala Lys Ser Arg Val His Pro Leu
545                 550

<210> SEQ ID NO 92
<211> LENGTH: 554
<212> TYPE: PRT
<213> ORGANISM: erythrovirus

<400> SEQUENCE: 92

Met Thr Ser Val Asn Ser Ala Glu Ala Ser Thr Gly Ala Gly Gly Gly
1               5                   10                  15

Gly Ser Asn Pro Thr Lys Ser Met Trp Ser Glu Gly Ala Thr Phe Thr
            20                  25                  30

Ala Asn Ser Val Thr Cys Thr Phe Ser Arg Gln Phe Leu Ile Pro Tyr
        35                  40                  45

Asp Pro Glu His His Tyr Lys Val Phe Ser Pro Ala Ala Ser Ser Cys
    50                  55                  60

His Asn Ala Ser Gly Lys Glu Ala Lys Val Cys Thr Ile Ser Pro Ile
65                  70                  75                  80

Met Gly Tyr Ser Thr Pro Trp Arg Tyr Leu Asp Phe Asn Ala Leu Asn
                85                  90                  95

Leu Phe Phe Ser Pro Leu Glu Phe Gln His Leu Ile Glu Asn Tyr Gly
            100                 105                 110

Ser Ile Ala Pro Asp Ala Leu Thr Val Thr Ile Ser Glu Ile Ala Val
        115                 120                 125

Lys Asp Val Thr Asp Lys Thr Gly Gly Gly Val Gln Val Thr Asp Ser
    130                 135                 140

Thr Thr Gly Arg Leu Cys Met Leu Val Asp His Glu Tyr Lys Tyr Pro
145                 150                 155                 160

Tyr Val Leu Gly Gln Gly Gln Asp Thr Leu Ala Pro Glu Leu Pro Ile
                165                 170                 175

Trp Val Tyr Phe Pro Pro Gln Tyr Ala Tyr Leu Thr Val Gly Glu Val
            180                 185                 190

Asn Thr Gln Gly Ile Ser Gly Asp Ser Lys Lys Leu Ala Ser Glu Glu
        195                 200                 205

Ser Ala Phe Tyr Val Leu Glu His Ser Ser Phe Glu Leu Leu Gly Thr
    210                 215                 220

Gly Gly Ser Ala Thr Met Ser Tyr Lys Phe Pro Ala Val Pro Pro Glu
225                 230                 235                 240

Asn Leu Glu Gly Cys Ser Gln His Phe Tyr Glu Met Tyr Asn Pro Leu
                245                 250                 255
```

| | | | | | | | | | | | | |
|---|---|---|---|---|---|---|---|---|---|---|---|---|
|Tyr|Gly|Ser|Arg|Leu|Gly|Val|Pro|Asp|Thr|Leu|Gly|Gly|Asp|Pro|Lys|
| | | |260| | | |265| | | |270| |

Tyr Gly Ser Arg Leu Gly Val Pro Asp Thr Leu Gly Gly Asp Pro Lys
                260                 265                 270

Phe Arg Ser Leu Thr His Glu Asp His Ala Ile Gln Pro Gln Asn Phe
        275                 280                 285

Met Pro Gly Pro Leu Ile Asn Ser Val Ser Thr Lys Glu Gly Asp Asn
290                 295                 300

Ser Asn Thr Gly Ala Gly Lys Ala Leu Thr Gly Leu Ser Thr Gly Thr
305                 310                 315                 320

Ser Gln Asn Thr Arg Ile Ser Leu Arg Pro Gly Pro Val Ser Gln Pro
                325                 330                 335

Tyr His His Trp Asp Thr Asp Lys Tyr Val Thr Gly Ile Asn Ala Ile
                340                 345                 350

Ser His Gly Gln Thr Thr Tyr Gly Asn Ala Glu Asp Lys Glu Tyr Gln
                355                 360                 365

Gln Gly Val Gly Arg Phe Pro Asn Glu Lys Glu Gln Leu Lys Gln Leu
370                 375                 380

Gln Gly Leu Asn Met His Thr Tyr Phe Pro Asn Lys Gly Thr Gln Gln
385                 390                 395                 400

Tyr Thr Asp Gln Ile Glu Arg Pro Leu Met Val Gly Ser Val Trp Asn
                405                 410                 415

Arg Arg Ala Leu His Tyr Glu Ser Gln Leu Trp Ser Lys Ile Pro Asn
                420                 425                 430

Leu Asp Asp Ser Phe Lys Thr Gln Phe Ala Ala Leu Gly Gly Trp Gly
                435                 440                 445

Leu His Gln Pro Pro Pro Gln Ile Phe Leu Lys Ile Leu Pro Gln Ser
        450                 455                 460

Gly Pro Ile Gly Gly Ile Lys Ser Met Gly Ile Thr Thr Leu Val Gln
465                 470                 475                 480

Tyr Ala Val Gly Ile Met Thr Val Thr Met Thr Phe Lys Leu Gly Pro
                485                 490                 495

Arg Lys Ala Thr Gly Arg Trp Asn Pro Gln Pro Gly Val Tyr Pro Pro
                500                 505                 510

His Ala Ala Gly His Leu Pro Tyr Val Leu Tyr Asp Pro Thr Ala Thr
                515                 520                 525

Asp Ala Lys Gln His His Arg His Gly Tyr Glu Lys Pro Glu Glu Leu
                530                 535                 540

Trp Thr Ala Lys Ser Arg Val His Pro Leu
545                 550

<210> SEQ ID NO 93
<211> LENGTH: 396
<212> TYPE: DNA
<213> ORGANISM: erythrovirus
<220> FEATURE:
<221> NAME/KEY: CDS
<222> LOCATION: (1)..(396)
<223> OTHER INFORMATION: Encodes amino acids 555-686 of SEQ ID NO: 2.

<400> SEQUENCE: 93 cct tta aat tgg gac ctc gaa agg cta ctg gaa ggt gga atc ccc agc         48
Pro Leu Asn Trp Asp Leu Glu Arg Leu Leu Glu Gly Gly Ile Pro Ser
1               5                   10                  15 ctg gcg ttt atc ctc ctc atg cag ctg gtc att tac cat atg tac tgt         96
Leu Ala Phe Ile Leu Leu Met Gln Leu Val Ile Tyr His Met Tyr Cys
            20                  25                  30 atg acc cca cag cta cag atg caa agc aac acc aca gac acg gat atg        144
Met Thr Pro Gln Leu Gln Met Gln Ser Asn Thr Thr Asp Thr Asp Met

```
                   35                  40                  45
aaa agc ctg aag aat tgt gga ctg cca aaa gcc gtg tgc acc cat tgt    192
Lys Ser Leu Lys Asn Cys Gly Leu Pro Lys Ala Val Cys Thr His Cys
 50                  55                  60 aaa cat tcc cca ccg tgt cct cag cca gga acc gtc acc cac cgc cca    240
Lys His Ser Pro Pro Cys Pro Gln Pro Gly Thr Val Thr His Arg Pro
 65                  70                  75                  80 cct gtg ccg ccc aga tta tat gtg ccc cct cca ata ccc cgt agg caa    288
Pro Val Pro Pro Arg Leu Tyr Val Pro Pro Pro Ile Pro Arg Arg Gln
                 85                  90                  95 cca tct ata aaa gat aca gac gct gta gaa tat aaa tta tta act aga    336
Pro Ser Ile Lys Asp Thr Asp Ala Val Glu Tyr Lys Leu Leu Thr Arg
            100                 105                 110 tat gaa caa cat gta att aga atg cta aga tta tgt aat atg tac aca    384
Tyr Glu Gln His Val Ile Arg Met Leu Arg Leu Cys Asn Met Tyr Thr
        115                 120                 125 agt ttg gaa aaa                                                    396
Ser Leu Glu Lys
    130

<210> SEQ ID NO 94
<211> LENGTH: 132
<212> TYPE: PRT
<213> ORGANISM: erythrovirus

<400> SEQUENCE: 94

Pro Leu Asn Trp Asp Leu Glu Arg Leu Leu Glu Gly Gly Ile Pro Ser
1               5                   10                  15

Leu Ala Phe Ile Leu Leu Met Gln Leu Val Ile Tyr His Met Tyr Cys
            20                  25                  30

Met Thr Pro Gln Leu Gln Met Gln Ser Asn Thr Thr Asp Thr Asp Met
        35                  40                  45

Lys Ser Leu Lys Asn Cys Gly Leu Pro Lys Ala Val Cys Thr His Cys
 50                  55                  60

Lys His Ser Pro Pro Cys Pro Gln Pro Gly Thr Val Thr His Arg Pro
 65                  70                  75                  80

Pro Val Pro Pro Arg Leu Tyr Val Pro Pro Pro Ile Pro Arg Arg Gln
                 85                  90                  95

Pro Ser Ile Lys Asp Thr Asp Ala Val Glu Tyr Lys Leu Leu Thr Arg
            100                 105                 110

Tyr Glu Gln His Val Ile Arg Met Leu Arg Leu Cys Asn Met Tyr Thr
        115                 120                 125

Ser Leu Glu Lys
    130

<210> SEQ ID NO 95
<211> LENGTH: 40
<212> TYPE: PRT
<213> ORGANISM: erythrovirus

<400> SEQUENCE: 95

Met Ser Lys Thr Thr Asn Lys Trp Trp Glu Ser Ser Asp Lys Phe Ala
1               5                   10                  15

Gln Asp Val Tyr Lys Gln Phe Val Gln Phe Tyr Glu Lys Ala Thr Gly
            20                  25                  30

Thr Asp Leu Glu Leu Ile Gln Ile
        35                  40

<210> SEQ ID NO 96
```

```
<211> LENGTH: 21
<212> TYPE: PRT
<213> ORGANISM: erythrovirus

<400> SEQUENCE: 96

Ser Leu Phe Asp Leu Val Ala Arg Ile Lys Ser Asn Leu Lys Asn Ser
1               5                   10                  15

Pro Asp Leu Tyr Ser
            20

<210> SEQ ID NO 97
<211> LENGTH: 24
<212> TYPE: PRT
<213> ORGANISM: erythrovirus

<400> SEQUENCE: 97

Leu Ser Asp His Pro His Ala Leu Ser Ser Asn Ser Ser Ala Glu
1               5                   10                  15

Pro Arg Gly Glu Asn Ala Val Leu
            20

<210> SEQ ID NO 98
<211> LENGTH: 21
<212> TYPE: PRT
<213> ORGANISM: erythrovirus

<400> SEQUENCE: 98

Glu Asp Leu His Lys Pro Gly Gln Val Ser Ile Gln Leu Pro Gly Thr
1               5                   10                  15

Asn Tyr Val Gly Pro
            20

<210> SEQ ID NO 99
<211> LENGTH: 22
<212> TYPE: PRT
<213> ORGANISM: erythrovirus

<400> SEQUENCE: 99

Gly Asn Glu Leu Gln Ala Gly Pro Pro Gln Asn Ala Val Asp Ser Ala
1               5                   10                  15

Ala Arg Ile His Asp Phe
            20

<210> SEQ ID NO 100
<211> LENGTH: 21
<212> TYPE: PRT
<213> ORGANISM: erythrovirus

<400> SEQUENCE: 100

Ile Lys Asn Glu Thr Gly Phe Gln Ala Gln Ala Val Lys Asp Tyr Phe
1               5                   10                  15

Thr Leu Lys Gly Ala
            20

<210> SEQ ID NO 101
<211> LENGTH: 32
<212> TYPE: PRT
<213> ORGANISM: erythrovirus

<400> SEQUENCE: 101

Ser Thr Gly Ala Gly Gly Gly Gly Ser Asn Pro Thr Lys Ser Met Trp
1               5                   10                  15

Ser Glu Gly Ala Thr Phe Thr Ala Asn Ser Val Thr Cys Thr Phe Ser
```

<210> SEQ ID NO 102
<211> LENGTH: 21
<212> TYPE: PRT
<213> ORGANISM: erythrovirus

<400> SEQUENCE: 102

Pro Pro Gln Tyr Ala Tyr Leu Thr Val Gly Glu Val Asn Thr Gln Gly
1               5                   10                  15

Ile Ser Gly Asp Ser
            20

<210> SEQ ID NO 103
<211> LENGTH: 37
<212> TYPE: PRT
<213> ORGANISM: erythrovirus

<400> SEQUENCE: 103

Ala Phe Tyr Val Leu Glu His Ser Ser Phe Glu Leu Leu Gly Thr Gly
1               5                   10                  15

Gly Ser Ala Thr Met Ser Tyr Lys Phe Pro Ala Val Pro Pro Glu Asn
            20                  25                  30

Leu Glu Gly Cys Ser
        35

<210> SEQ ID NO 104
<211> LENGTH: 28
<212> TYPE: PRT
<213> ORGANISM: erythrovirus

<400> SEQUENCE: 104

Gln Asn Phe Met Pro Gly Pro Leu Ile Asn Ser Val Ser Thr Lys Glu
1               5                   10                  15

Gly Asp Asn Ser Asn Thr Gly Ala Gly Lys Ala Leu
            20                  25

<210> SEQ ID NO 105
<211> LENGTH: 19
<212> TYPE: DNA
<213> ORGANISM: erythrovirus

<400> SEQUENCE: 105
tgcagatgcc ctccaccca                                              19

<210> SEQ ID NO 106
<211> LENGTH: 21
<212> TYPE: DNA
<213> ORGANISM: erythrovirus

<400> SEQUENCE: 106
gctgctttca ctgagttctt c                                           21

<210> SEQ ID NO 107
<211> LENGTH: 20
<212> TYPE: DNA
<213> ORGANISM: erythrovirus

<400> SEQUENCE: 107
gaccagttca ggagaatcat                                             20

<210> SEQ ID NO 108
<211> LENGTH: 19

```
<212> TYPE: DNA
<213> ORGANISM: erythrovirus

<400> SEQUENCE: 108
atcggcaagc ggcgtgtaa                                               19

<210> SEQ ID NO 109
<211> LENGTH: 20
<212> TYPE: DNA
<213> ORGANISM: erythrovirus

<400> SEQUENCE: 109
atccagacag gtaagcacat                                              20

<210> SEQ ID NO 110
<211> LENGTH: 21
<212> TYPE: DNA
<213> ORGANISM: erythrovirus

<400> SEQUENCE: 110
atcggcaagc ggcgtgtaaa a                                            21

<210> SEQ ID NO 111
<211> LENGTH: 19
<212> TYPE: DNA
<213> ORGANISM: erythrovirus

<400> SEQUENCE: 111 catgcctat catccagta                                                19

<210> SEQ ID NO 112
<211> LENGTH: 20
<212> TYPE: DNA
<213> ORGANISM: erythrovirus

<400> SEQUENCE: 112
ttggctatac ctaaagtcat                                              20

<210> SEQ ID NO 113
<211> LENGTH: 19
<212> TYPE: DNA
<213> ORGANISM: erythrovirus

<400> SEQUENCE: 113
cactatgaaa actgggcaa                                               19

<210> SEQ ID NO 114
<211> LENGTH: 19
<212> TYPE: DNA
<213> ORGANISM: erythrovirus

<400> SEQUENCE: 114
acaattcttc atctgctac                                               19

<210> SEQ ID NO 115
<211> LENGTH: 21
<212> TYPE: DNA
<213> ORGANISM: erythrovirus

<400> SEQUENCE: 115
aaactgggca ataaactaca c                                            21

<210> SEQ ID NO 116
<211> LENGTH: 20
```

-continued

```
<212> TYPE: DNA
<213> ORGANISM: erythrovirus

<400> SEQUENCE: 116
cttcatctgc taccgtccaa                                               20

<210> SEQ ID NO 117
<211> LENGTH: 33
<212> TYPE: DNA
<213> ORGANISM: erythrovirus

<400> SEQUENCE: 117
aaaggcctag atcttgtaga ttatgagtaa aac                                33

<210> SEQ ID NO 118
<211> LENGTH: 26
<212> TYPE: DNA
<213> ORGANISM: erythrovirus

<400> SEQUENCE: 118
cggaattcgg tgggtgacgg ttcctg                                        26

<210> SEQ ID NO 119
<211> LENGTH: 29
<212> TYPE: DNA
<213> ORGANISM: erythrovirus

<400> SEQUENCE: 119
cacggatcca taccccagca tgacttcag                                     29

<210> SEQ ID NO 120
<211> LENGTH: 27
<212> TYPE: DNA
<213> ORGANISM: erythrovirus

<400> SEQUENCE: 120
cacggatccg gtgggtgacg gttcctg                                       27

<210> SEQ ID NO 121
<211> LENGTH: 36
<212> TYPE: DNA
<213> ORGANISM: erythrovirus

<400> SEQUENCE: 121
accagtatca gcagcagtgg tggtgaaagc tctgaa                             36
```

METHOD OF MAKING NOVEL ERYTHROVIRUS V9 VP2 CAPSID POLYPEPTIDES

The present application is a divisional application of U.S. patent application Ser. No. 09/555,640 (now U.S. Pat. No. 7,291,452), filed Aug. 10, 2000, which claims priority to French Patent Application 9715197, filed Dec. 3, 1997.

The present invention relates to nucleic sequences derived from a human erythrovirus, to their fragments as well as to their applications as diagnostic reagent and as an immunogenic agent.

Sero-epidemiological studies show that infection with the parvovirus B19, recently renamed erythrovirus B19, is commonly and widely distributed worldwide.

In Europe, the seroprevalence for erythrovirus B19 is about 10% in subjects under 5 years, about 50% for subjects over 20 years and greater than 90% in elderly persons.

The high seroprevalence rate suggests that erythrovirus B19 is highly contagious. During epidemics, the rate of transmission to subjects in close contact is 10 to 60%, the route of transmission being mainly aerial (respiratory secretions).

Erythrovirus B19 is a specifically human virus. Acute infection commonly causes benign maculopapular skin rashes in children (epidermal megalerythema or $5^{th}$ disease). Arthralgias may accompany the rashes and may exceptionally become chronic.

A transient acute erythroblastic attack usually occurs in patients already carrying a chronic haemolytic anaemia (sickle cell anaemia, thalassaemia, pyruvate kinase deficiency and the like), causing a transient aregenerative acute anaemia.

Acute primary infection with erythrovirus B19 is particularly dangerous in pregnant women with a risk of transmission to the fetus estimated at 30%. The risk of foetal death by anaemia, hepatic insufficiency, cardiac insufficiency and foetoplacental anasarca is estimated at between 5 and 9%.

Chronic infections with erythrovirus B19 are found essentially in immunosuppressed subjects (chronic myeloid leukaemia, humoral and cellular immune deficiency, organ or marrow transplants, AIDS diseases).

In seropositive HIV-1 patients, chronic infection with erythrovirus B19 is responsible for chronic anaemia, but can also act on the other lineages (neutropenia and especially thrombopenia). The absence of a sufficient humoral immune response in these patients allows the installation of a chronic erythroviraemia and explains both the chronic erythroblastopenia and the absence of other symptoms such as rash or arthralgias.

Erythrovirus B19 is a virus having a single-stranded DNA genome of about 5.4 kbases; it is the only erythrovirus classified to date; all the strains which have been sequenced and which have been the subject of a publication in the sequence libraries (GenBank or EMBL) exhibit a low genetic variability (98% nucleic sequence similarity over the whole genome and 96% similarity over the VP1 region) (R. O. SHADE, J. Virol., 1986, 58, 3, 921-936, B19-AU).

Virological diagnosis of erythrovirus B19 infections is based essentially on the detection of the viral genome, insofar as the culture cannot be carried out routinely.

For acute infections with erythrovirus B19 (primary infections), this detection can be made by gene amplification (PCR), but also be hybridization (dot-blot) given the viral titre, which is usually very high during primary infections (up to $10^{14}$/ml of serum); however, the viral titre is much lower during chronic infections and only a gene amplification detection method can be envisaged.

These detection techniques are dependent on the genetic variability of the virus tested for; the reagents prepared from known erythrovirus B19 sequences do not make it possible to detect the variant erythro-virus infections, either by gene amplification or by B19 serodiagnosis.

Indeed, the existing serodiagnostic tests are specific for erythrovirus B19 (International Application PCT WO 91/12269; International Application POT WO 96/09391 (IDEIA® Parvovirus B19 IgG and IgM, DAKO; Parvovirus B19 IgG and IgM Enzyme Immunoassay, BIOTRIN)).

Consequently, the detection techniques specified above risk producing negative results both at the nucleic level and with respect to the antibody response.

The identification and the taking into account of new variants are important for developing:
reagents for the detection and diagnosis of human erythrovirus infections (serodiagnosis, PCR, hybridization), which are sufficiently sensitive and specific, that is to say which do not lead to false-negative or false-positive results,
compositions capable of protecting against all erythrovirus infections (vaccines), and
compositions capable of treating a variant erythrovirus infection (serotherapy, monoclonal anti-bodies).

The inventors therefore set themselves the aim of providing erythrovirus-derived sequences capable of allowing the detection of a variant erythrovirus (called erythrovirus type V9), that is to say which is genetically distant from erythrovirus B19.

The subject of the present invention is a nucleic acid sequence, characterized in that it is selected from the group consisting of:
the sequences derived from an erythrovirus which, molecularly, cannot be recognized as an erythro-virus B19 because it exhibits a genetic divergence or distance $\geq$10% (<90% similarity) over the whole genome with respect to the erythrovirus B19 sequences and which exhibit a genetic divergence of less than or equal to 6% (>94% similarity) with respect to the sequence SEQ ID NO:1,
the sequence SEQ ID NO:1, and
the nucleotide sequences capable of hybridizing under stringent conditions with the said sequence ID NO:1.

This variant erythrovirus is called type V9 variant.

Stringent conditions are understood to mean, for the purposes of the present invention, the following conditions:
hybridization for 3 to 24 h in a 1×SSC buffer containing 50% formamide, at 42° C., and
3 washes of 15 min in a 2×SSC buffer, at 60° C.

The sequence SEQ ID NO:1, which corresponds to about 95% of the genome of an erythrovirus type V9 and which includes all the coding sequences, has a restriction map which is different from that of the B19 erythroviruses, in particular as regards the BamHII site (no site), HINDIII site (only one site) and PvuII site (five sites).

More precisely, the sequence SEQ ID NO: 1 has a restriction profile which is different from that of erythrovirus B19, in particular by the following restriction sites: AccI, AflIII, AlwI, AlwNI, ApaI, AvaI, AvaII, AvrII, BamHI, BanI, BanII, SbeI, BbsI, BceFI, BcgI, BcnI, BglII, BsgI, BsiEI, BsmI, BsmAI, Bsp120I, BspHI, BspMI, BsrFI, Bst1107I, BstEII, BstUI, Bsu36I, DpnI, DraIII, DsaI, EaeI, EagI, EarI, Ec1136I, EcoNI, Eco109I, EcoRI, EheI, FokI, HaeI, HaeIII, HgaI, HgiAI, HhaI, HincII, HindIII, HinPI, HpaI, KasI, MaeII, MboI, McrI, MscI, MunI, NarI, NciI, NcoI, NsiI, NspI, Nsp7524I, NspBII, NspCI, PflMI, PmeI, Ppu10I, PpuMI, stI, PvuII, SacI, Sau3AI, Scal, SfaNI, SfcI, SmaI, peI, SphI, SspI, StuI, StyI, SwaI, Tth111I, XbaI, XmaI and their isoschizomers.

The subject of the present invention is also fragments of sequence ID NO:1 which are capable of allowing the detection of an erythrovirus V9 and characterized in that they comprise a nucleotide sequence selected from the group consisting of:

a) a sequence corresponding to positions 328-2340 of SEQ ID NO:1, encoding the NS1 protein (SEQ ID NO:81),
b) a sequence corresponding to positions 1796-2017 of SEQ ID NO:1, encoding the 7.5 kDa protein (SEQ ID NO:83),
c) a sequence corresponding to positions 2336-4678 of SEQ ID NO:1, encoding the VP1 protein (SEQ ID NO:85),
d) a sequence corresponding to positions 2336-3016 of SEQ ID NO:1, encoding the VP1u (SEQ ID NO:87),
e) a sequence corresponding to positions 2523-2828 of SEQ ID NO:1, encoding the X protein (SEQ ID NO:89),
f) a sequence corresponding to positions 3017-4678 of SEQ ID NO:1, encoding the VP2 (SEQ ID NO:91),
g) a sequence corresponding to positions 4488-4883 of SEQ ID NO:1, encoding the 11 kDa protein (SEQ ID:93),
h) a nucleotide sequence capable of hybridizing with one of the sequences SEQ ID NO:1, SEQ ID NO:81, SEQ ID NO:83, SEQ ID NO:85, SEQ ID NO:87, SEQ ID NO:89, SEQ ID NO:91 or SEQ ID NO:93,
i) the sequences SEQ ID NO:2-80,
j) the sequences SEQ ID NO:105 (E105f), 106 (E1987r), 107 (E2076f), 108 (E2151r), 109 (E2406r), 110 (E2149rs), 111 (E2717f), 112 (E2901r), 113 (e1855f), 114 (e2960r), 115 (e1863f), 116 (e2953), 117 (e2435fStul/BglII), 118 (e4813rEcoRI), 119 (e3115fBamHI), 120 (e4813rBamHI) and 121 (e1954fp) and k) the sequences complementary to the preceding sequences, the fragments derived from the preceding sequences of at least 17 nucleotides or their complementary sequences.

For the purposes of the present invention, nucleic sequence or nucleotide sequence (DNA or RNA sequence) is understood to mean one of the sequences as defined above and their complementary sequences (anti-sense sequences) as well as the sequences comprising one or more of the said sequences or fragments thereof.

The invention also includes nucleotide fragments complementary to the preceding ones as well as fragments modified with respect to the preceding ones by removal or addition of nucleotides in a proportion of about 15%, with respect to the length of the above fragments and/or modified at the level of the nature of the nucleotides, as long as the modified nucleotide fragments retain a capacity for hybridization with the erythrovirus V9 DNA or RNA sequence which is similar to that exhibited by the corresponding unmodified fragments.

Some of these fragments are specific and are used as a probe or primer; they hybridize specifically to an erythrovirus V9 or a related erythrovirus; a virus related to erythrovirus V9 is understood to mean an erythrovirus exhibiting a genetic divergence of less than or equal to 6%; these fragments are selected from the group consisting of the sequences SEQ ID NO:45-80 and NO:108 and 110, or their complementary sequences, the sequences derived from these sequences of at least 17 nucleotides and the sequences comprising the said sequences and they find application in the specific identification of an erythrovirus V9 or of a related erythrovirus.

Others of these fragments are used as primers, for the amplification of sequences derived from an erythrovirus type V9 or a related virus, such as the sequence SEQ ID NO:1; these primers are chosen from the group consisting of the sequences SEQ ID NO:2-44 and the sequences SEQ ID NO:105-109 and 111-121 or their complementary sequences and the sequences derived from the said sequences, of at least 17 nucleotides.

The said fragments also include, in the case of primers, the antisense sequences.

Such sequences find application for the differential identification of erythroviruses (erythrovirus B19 and erythrovirus V9), combined with probes as defined above and/or with suitable restriction enzymes.

The said primers preferably comprise between 17 and 30 nucleotides; preferred primers are the following: the sequence SEQ ID NO:105 (positions 1797-1815 of the sequence SEQ ID NO:1, which corresponds to the sequence SEQ ID NO:10, the sequence SEQ ID NO:106 (positions 1899-1879 of the sequence SEQ ID NO:1), which corresponds to a fragment of the antisense sequence of the sequence SEQ ID NO:11, the sequence SEQ ID NO:107 (positions 1968-1987 of the sequence SEQ ID NO:1), which corresponds to a fragment of the sequence SEQ ID NO:13, the sequence SEQ ID NO:108 (positions 2061-2043 of the sequence SEQ ID NO:1), which corresponds to a fragment of the antisense sequence of the sequence SEQ ID NO:58, the sequence SEQ ID NO:109 (positions 2317-2298 of the sequence SEQ ID NO:1), which corresponds to a fragment of the antisense sequence of the sequence SEQ ID NO:16, the sequence SEQ ID NO:111 (positions 2609-2627 of the sequence SEQ ID NO:1), which corresponds to a fragment of the sequence SEQ ID NO:19 and the sequence SEQ ID NO:112 (positions 2812-2793 of the sequence SEQ ID NO:1), which corresponds to a fragment of the antisense sequence of the sequence SEQ ID NO:23.

Preferred pairs of primers are the following:
pair A: primers SEQ ID NO:111 and SEQ ID NO:112;
pair B: primers SEQ ID NO:105 and SEQ ID NO:106;
pair C: one of the sequences SEQ ID NO:2-44, 105, 106, 107, 109, 111 or 112 and one of the sequences SEQ ID NO:45-80, 108 or 110;
pair D: primer SEQ ID NO:107 and primer SEQ ID NO:109;
pair E: two primers selected from the sequences SEQ ID NO:2-44, 105, 106, 107, 109, 111 or 112;
pair F: two primers selected from the sequences SEQ ID NO:45-80, 103 or 110.

These various primers can be used, depending on the fragment amplified, as sense primer or as antisense primer.

The subject of the present invention is also a variant erythrovirus, characterized in that its genome cannot be recognized molecularly as an erythrovirus B19, in that it exhibits a divergence of less than or equal to 6% with the sequence SEQ ID NO:1, as defined above, and in that its genome hybridizes specifically, under stringent conditions, as defined above, with one of the sequences SEQ ID NO:45 to 80, 108 and 110, as defined above.

The subject of the present invention is also a plasmid, characterized in that it comprises the viral genome of a variant erythrovirus strain, called erythrovirus V9 or a fragment thereof, which cannot be recognized molecularly as an erythrovirus B19 and which exhibits with the latter a genetic divergence of ≧10% over the whole genome with respect to the erythrovirus B19 sequences and a divergence of less than or equal to 6% with the sequence SEQ ID NO:1.

The viral genome of the said erythrovirus V9 is considered to be genetically distant from erythrovirus B19.

According to an advantageous embodiment of the said plasmid, it includes the sequence SEQ ID NO:1 (PCD.V9.C22).

The subject of the present invention is also a diagnostic reagent for the differential detection of type V9 erythroviruses, characterized in that it is selected from the sequences SEQ ID NO:45-80, 108 and 110, optionally labelled with an appropriate marker.

Among the appropriate markers, there may be mentioned radioactive isotopes, enzymes, fluorochromes, chemical markers (biotin and the like), haptens (digoxygenin and the like) and antibodies or appropriate base analogues.

The subject of the present invention is also a process for the rapid and differential detection of erythroviruses, by hybridization and/or gene amplification, using a biological sample as starting material, which process is characterized in that it comprises:

(1) a step in which a biological sample to be analysed is brought into contact with at least one probe of sequence SEQ ID NO:45-80, 108 or 110, and (2) a step in which the product(s) resulting from the erythrovirus nucleotide sequence-probe interaction is (are) detected by any appropriate means.

Preferably, the hybridization comprises a pre-hybridization which is carried out in a buffer which comprises 5-60% of formamide; 1-5×SSC; 2% of blocking reagent (Blocking buffer, Boehringer Mannheim, Meylan, France); 0.1% of N-laurylsarcosine; 0.01-5% of SDS, at 40-70° C. for 90 minutes, and then the hybridization is carried out in 3 ml of a buffer of the same composition with 10 μl of labelled probe at 40-70° C. for 1-30 hours.

In accordance with the said process, it may comprise, prior to step (1);

- a step extracting the nucleic acid to be detected, belonging to the virus genome, which may be present in the biological sample, and
- at least one gene amplification cycle.

The gene amplification step is in particular carried out with the aid of one of the following gene amplification techniques: amplification with Qβ-replicase (I. Haruna et al., Proc. Nat. Acad. Sci. USA, 1965, 54, 579-587), PCR (polymerase chain reaction) (R. K. Saiki et al., 1986, Nature, 324:163-6), LCR (ligase chain reaction) (F. Barany, Proc. Nat. Acad. Sci. USA, 1991, 88, 189-193), ERA (end-run amplification) (C. Adams et al., 1994, *Novel amplification technologies for DNA/RNA-based diagnostics meeting*, San Francisco, Calif., United States), CPR (cycling probe reaction) (P. Duck et al., Biotechniques, 1990, 9, 142-147) or SDA (strand displacement amplification) (GT. Walker, 1994, *SDA: novel amplification technologies for DNA/RNA-based diagnostics meeting*, San Francisco, Calif., United States).

According to an advantageous embodiment of the said process, the amplification cycles are carried out with the aid of a pair of primers selected from the sequences SEQ ID NO:2-44, 105-109 and 111-112 and fragments of these sequences, preferably from the pairs of primers as defined above.

When pair A is used, the amplification product is advantageously screened by the action of the restriction enzyme ApaI (GGGCCC): the product of amplification of a B19 genome is cleaved with ApaI (generating 2 fragments of 149 and 55 base pairs (bp)) whereas the product of amplification of a V9 genome is not cleaved by ApaI (a fragment of 204 bp); an agarose or acrylamide gel electrophoresis makes it possible to distinguish between these restriction fragments.

When pair B is used, the product of amplification is advantageously screened by the action of one of the following restriction enzymes: BglII (AGATCT), or MunI (CAATTG); different fragments are thus obtained depending on whether an erythrovirus V9 or B19 is involved; a fragment which comprises a BglII restriction site is specific for the variant erythrovirus V9 as defined above, whereas the B19 erythroviruses comprise an MunI site in this region. The product of amplification of a B19 genome is cleaved with MunI (generating 2 fragments of 36 and 67 bp) and is not cleaved by BglII (a fragment of 103 bp) whereas the product of amplification of a V9 genome is cleaved by BglII (2 fragments of 19 and 84 bp) and is not cleaved by MunI (a fragment of 103 bp); an agarose or acrylamide gel electrophoresis makes it possible to distinguish between these different restriction fragments.

When pair C is used (a primer capable of hybridizing with all erythroviruses and a primer capable of specifically hybridizing with erythrovirus V9) or when pair F is used (two primers capable of specifically hybridizing with erythrovirus V9), the V9 genome is amplified whereas there is no specific amplification with the B19 genome.

When pair D is used, the product of amplification is advantageously screened by hybridization with a labelled specific probe for erythrovirus V9, selected from the sequences SEQ ID NO:58-60 and 110, preferably by hybridization with the probe of sequence SEQ ID NO:110; the product of amplification of a V9 genome hybridizes specifically with these probes and in particular the probe of sequence SEQ ID NO:110, whereas the product of amplification of a B19 genome does not hybridize with the abovementioned probes.

When pair E is used, the product of amplification is screened by any method of hybridization with a probe specific for erythrovirus V9, selected from the sequences SEQ ID NO:45-80, 108 and 110; in this case, the product of amplification of a V9 genome hybridizes with the probe, but not the product of amplification of a B19 genome.

The subject of the invention is also the use of the sequences described above, of fragments derived from these sequences or of their complementary sequences, for carrying out a method of hybridization or of gene amplification of erythrovirus nucleic sequences, these methods being applicable to the in vitro diagnosis of the potential infection of an individual with an erythrovirus type V9.

The subject of the present invention is also a method of screening and typing an erythrovirus V9 or a related virus, characterized in that it comprises bringing a probe selected from the group consisting of the sequences SEQ ID NO:45-80, 108 and 110, optionally labelled, into contact with the nucleic acid of the virus to be typed and detecting the nucleic acid-probe hybrid obtained.

The subject of the present invention is also products of translation, characterized in that they are encoded by a nucleotide sequence as defined above.

The subject of the present invention is also a protein, characterized in that it is in particular capable of being expressed with the aid of a nucleotide sequence selected from the group consisting of the sequences SEQ ID NO:81, 83, 85, 87, 89, 91 and 93, as defined above and the derived peptides comprising between 7 and 50 amino acids.

Peptide is understood to mean below both the proteins and the peptides, as defined above.

Such peptides are in particular capable of being recognized by antibodies induced by an erythro-virus V9 and/or of inducing the production of anti-erythrovirus V9 antibodies.

The said peptides are in particular selected from the sequences SEQ ID NO:82 (NS1 protein), SEQ ID NO:86 (VP1 protein), SEQ ID NO:88 (single VP1 protein), SEQ ID NO:92 (VP2 protein) and SEQ ID NO:95-104, namely fragments of the VP1 protein [VP1a peptide (SEQ ID NO:95); VP1b peptide (SEQ ID NO:96); VP1c peptide (SEQ ID NO:97); peptide VP1d (SEQ ID NO:98); peptide VP1e (SEQ ID NO:99) and peptide VP1f (SEQ ID NO:100)], or fragments of the VP2 protein [peptide VP2a (SEQ ID NO:101); peptide VP2b (SEQ ID NO:102); peptide VP2c (SEQ ID NO:103); peptide VP2d (SEQ ID NO:104)] as well as the derived peptides comprising 7 to 50 amino acids.

The subject of the invention is also immuno-genic compositions comprising one or more products of translation of the nucleotide sequences according to the invention and/or one or the peptides as defined above, obtained in particular by synthetic means.

The subject of the invention is also the anti-bodies directed against one or more of the peptides described above and their use for carrying out in particular a differential in vitro method of diagnosis of the infection of an individual with an erythrovirus.

The subject of the present invention is also a method for the immunological detection of an erythro-virus V9 infection, characterized in that it comprises:

for the detection of anti-erythrovirus V9 antibodies, bringing a biological sample into contact with a peptide according to the invention (serodiagnosis), for the detection of erythrovirus V9 viral proteins, bringing a biological sample into contact with an antibody according to the invention;

the reading of the result being revealed by an appropriate means, in particular EIA, ELISA, RIA, fluorescence.

By way of illustration, such an in vitro method of diagnosis according to the invention comprises bringing a biological sample, collected from a patient, into contact with antibodies according to the invention or peptides according to the invention, and detecting, with the aid of any appropriate method, in particular with the aid of labelled anti-immunoglobulins, immunological complexes formed between the antigens or the antibodies of the erythroviruses which may be present in the biological sample and the said antibodies or the said peptides, respectively.

The reagents according to the invention are in particular useful for the detection of the V9 erythro-viruses and related viruses in pregnant women, in HIV-positive patients with anaemia and/or chronic thrombopenia, recipients of organ or marrow trans-plants, and patients having a central acute anaemia and for whom the tests for the detection of erythrovirus B19 are negative.

The subject of the invention is, in addition, an erythrovirus diagnostic kit, characterized in that it includes at least one reagent according to the invention (probes, pairs of primers, peptides or anti-bodies).

In addition to the preceding features, the invention further comprises other features which will emerge from the description which follows, which refers to exemplary embodiments of the method which is the subject of the present invention as well as to the appended drawings, in which:

FIGS. 1, 2 and 3 illustrate phylogenetic trees for erythrovirus V9: FIG. 1: phylogenetic tree for the complete erythrovirus sequence; FIG. 2: phylogenetic tree for the erythrovirus NS1 genes; FIG. 3: phylogenetic tree for the erythrovirus VP1 genes;

FIGS. 4, 5 and 6 represent the genetic distances for the complete erythrovirus sequences (FIG. 4), for the erythrovirus NS1 genes (FIG. 5) and for the erythrovirus VP1 genes (FIG. 6);

FIG. 7 illustrates the restriction map of sequence ID NO:1.

Figure 1:
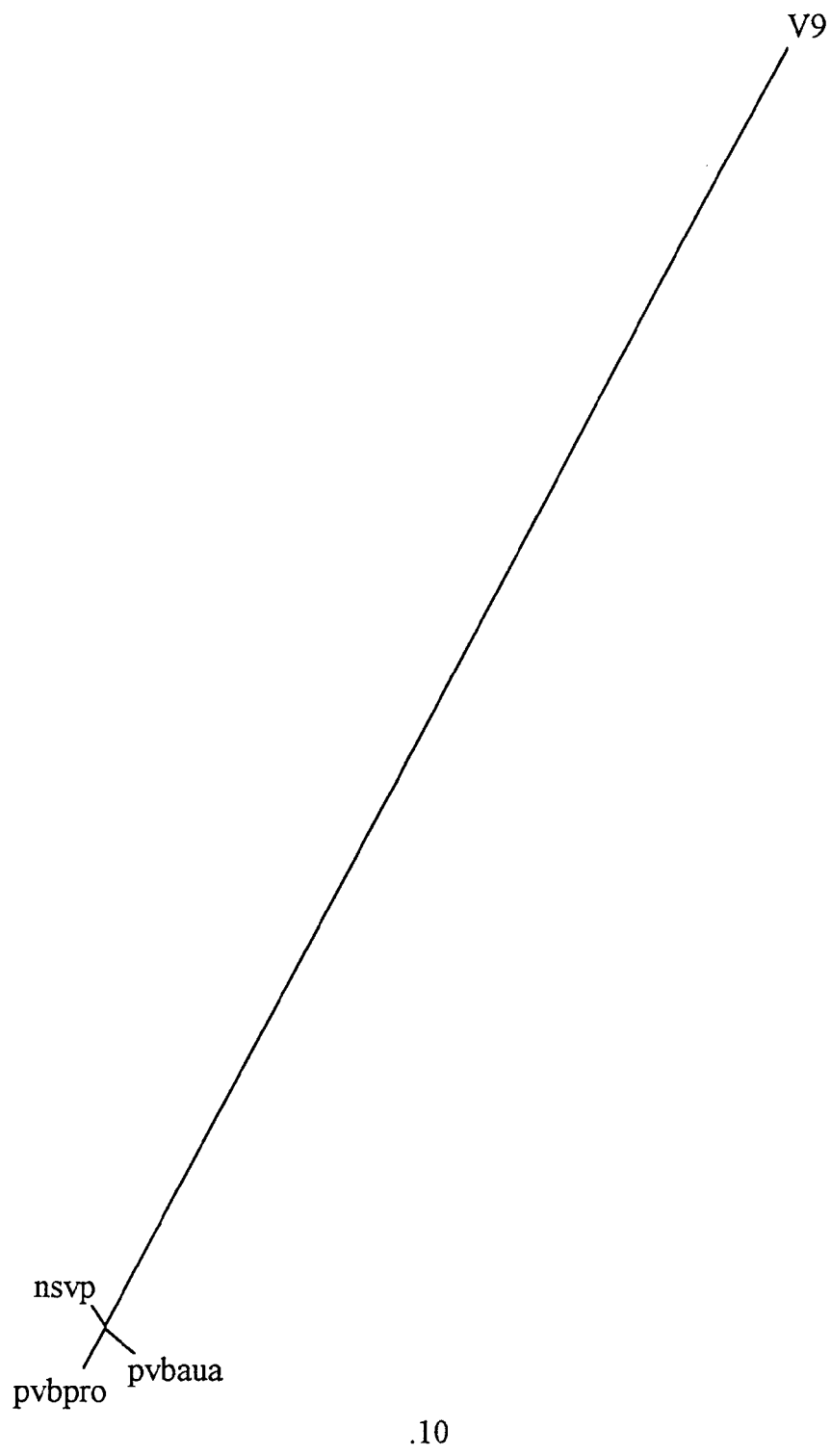

It should be understood, however, that these examples are given solely by way of illustration of the subject of the invention and do not constitute in any manner a limitation thereto.

EXAMPLE 1

Production of Sequences Conforming to the Invention

An AatII/AatII restriction fragment of 5028 hp, representing virtually the entire (95%) genome of the V9 variant, was cloned into the sequencing vector pcDNA2.1 (Invitrogen, Netherlands) in the following manner.

The single-stranded viral DNA was extracted from the serum of a patient with an acute erythro-blastopenic attack with the aid of a QIAamp Blood Kit column (Qiagen S.A., France). Using a step of hybridization in a 50 mM Nacl buffer at 56° C. for 16 hours, the viral DNA is converted to double-stranded DNA. Next, 1.3 µg of double-stranded viral DNA is subjected to the AatII restriction enzyme (18 U) at 37° C. for 2 hours, the restriction enzyme is then inactivated at 65° C. for 15 minutes. The product is dialysed on a Millipore VSWPO13000 cellulose acetate and nitrate membrane against water for 2 hours. The double-stranded viral DNA AatII/AatII restriction fragment thus prepared is frozen at −20° C. while awaiting the ligation step.

The vector pCDNA2.1 is modified in order to receive the AatII fragment by site-directed insertion mutation: the EagI restriction site of the multiple cloning site was removed and replaced with an AatII site. The vector pcDNA2.1a thus produced was amplified in bacterial culture and purified with the aid of a QIAfilter Plasmid Maxi Kit (Qiagen S.A., France). Next, 3 µg of the vector pcDNA2.1a is subjected to restriction with the enzyme AatII at 37° C. for 1 hour and then dephosphorylated with shrimp alkaline phosphatase (Boehringer Mannheim, Meylan, France). The enzymes are inactivated at 65° C. for 15 minutes.

The ligation is carried out with a vector/viral DNA insert molar ratio of 1/1, that is to say 50 ng of vector and 100 ng of viral DNA insert, prepared as described above, with the aid of 1 U of T4 ligase (Life Technologies, France) at 24° C. for 16 hours. After a ½ dilution, the ligation product is heated at 65° C. in order to inactivate the T4 ligase and then cooled on ice. Electrocompetent bacteria Sure® (Stratagene, Heidelberg, Germany) are electrophorized with 2 or 4 µl of this ligation solution (1500 V, 50 µF, 200Ω) and then incubated with 1 ml of SOC medium (Life Technologies, France) for 1 hour before being spread on a Luria Broth agar medium (Life Technologies, France) containing 100 µg/ml of amoxicillin, 15 µg/ml of tetra-cycline, 100 µg/ml of IPTG and 50 µg/ml of X-gal.

Twenty four (recombinant) white colonies were selected, their plasmid is extracted by minipreparation of DNA and a rough restriction map (AatII, AatII+BamHI, BamHI, BamHI+BglII, HindII) made it possible to select 2 recombinant clones with an insert having a size and a restriction map compatible with a V9 viral DNA insert.

These 2 clones (2 and 22) were sequenced with the aid of an automated sequencer ABI 377 (Perkin Elmer, France): they indeed contain an insert of 5028 bp, the 2 sequences are identified except at position 1165 (A and G for the clones 2 and 22 respectively). The direct sequence of the V9 viral DNA made it possible to determine that it is the G at position 1165 which is correct; it is therefore clone 22 which was selected (PCD.V9.C22), whose sequence corresponds to SEQ ID NO:1.

Figure 2:
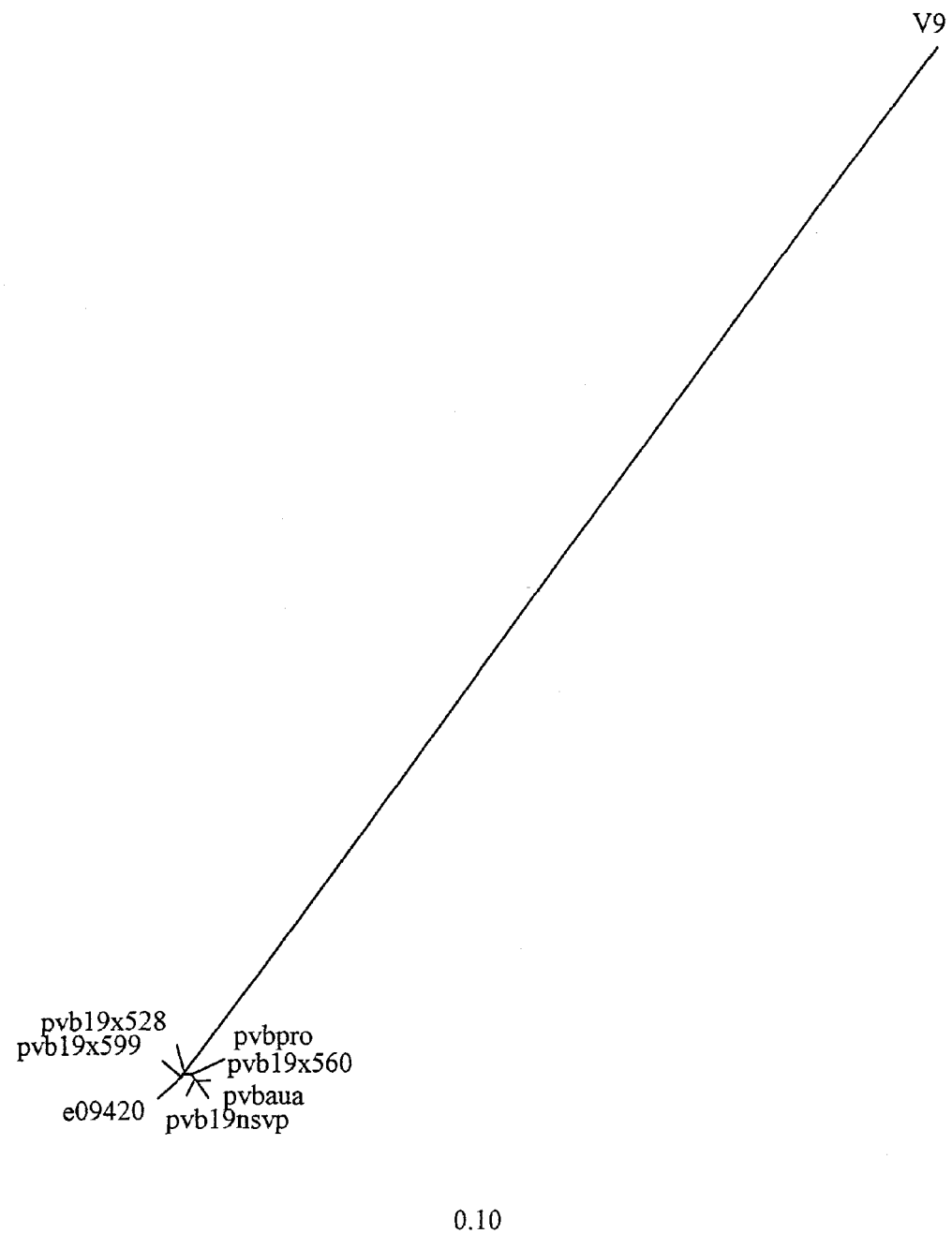
Figure 3:
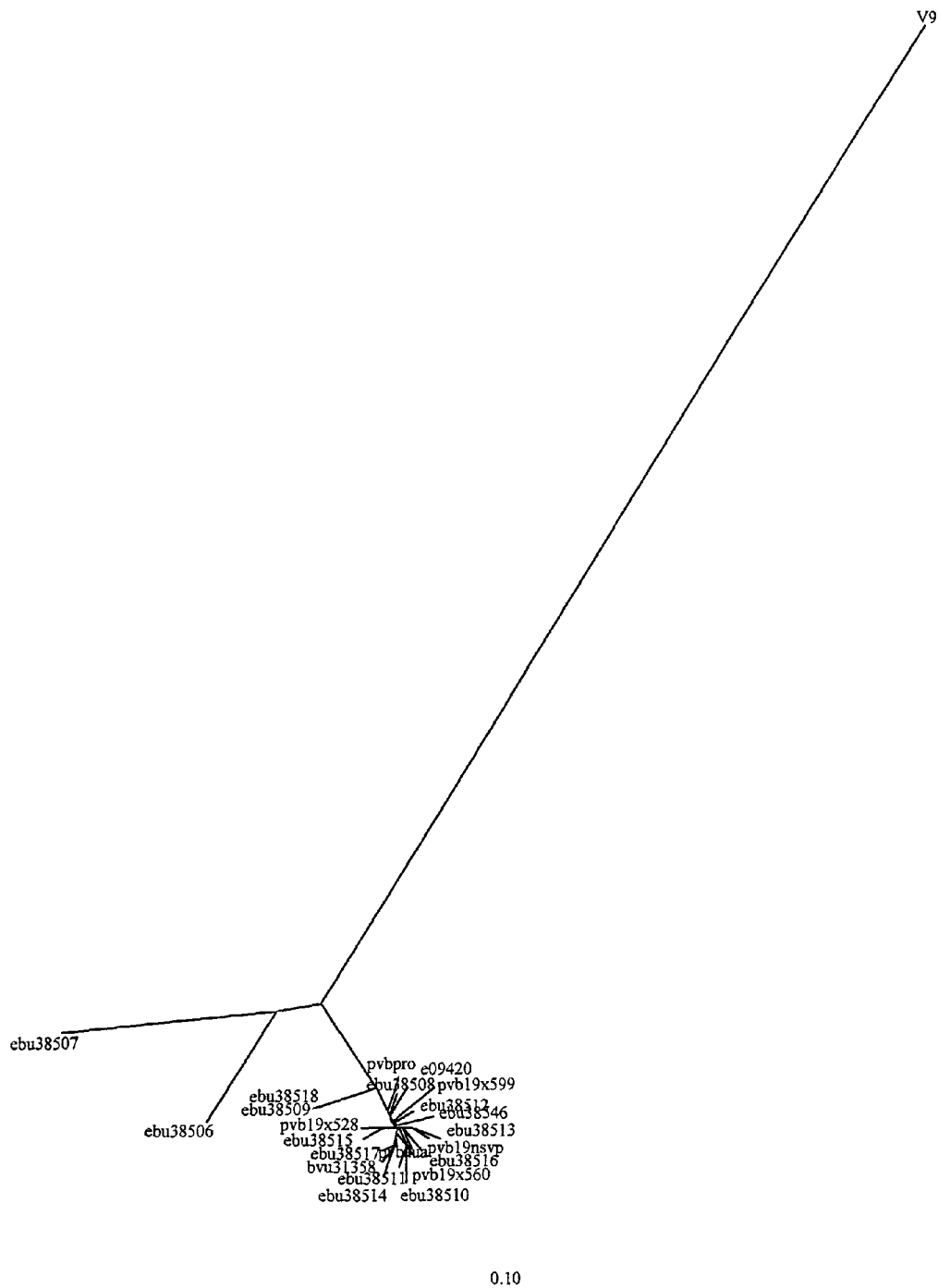

FIGS. 1 to 6 show the genetic distances which exist between erythrovirus V9 and erythrovirus B19. In these figures, the different erythrovirus sequences are represented by their mnemonic in GenBank (release 103.0 of October 1997).

EXAMPLE 2

Diagnosis of an Erythrovirus type V9 by DNA Hybridization (Dot Blot or Slot Blot or Microplate) with a Specific Probe The viral DNA is extracted, for example, with the aid of a QIAamp Blood Kit column (Qiagen S.A., France) or of any other method of extracting nucleic acids from a biological sample (blood, serum, plasma, amniotic fluid, bone marrow, tissue). The DNA in solution is denatured at 95° C. for 2 minutes and then cooled on ice, transferred onto nylon or cellulose nitrate membrane by vacuum filtration and then fixed (heating of the membrane at 80° C. for 1 hour). The membrane is then hybridized under stringent conditions with a DNA or RNA probe specific for V9, such as the sequence SEQ ID NO:1 or its complementary sequence or a fragment thereof, in particular the sequences SEQ ID NO:45 to SEQ ID NO:80 and 110 and their complementary sequences, or a fragment of these sequences which are appropriately labelled. This labelling may be a labelling with a radioelement ($^{32}$P, $^{33}$P, $^{35}$S, $^{3}$H, $^{14}$C or another radio isotope), a cold labelling (biotin), fluorescent marker, digoxygenin or any other molecule which may be coupled or incorporated into a DNA or RNA fragment and which can be detected by a specific antibody, or by a ruthenium chelate). In the case of a labelling with a radioactive element, the visualization is performed by autoradiography or any other method allowing the detection of the radioisotope emission (such as Phosphorimager, Molecular Dynamics, Bondoufle, France). In the case of a labelling with biotin, the visualization is performed with the aid of an enzyme/streptavidine conjugate and a suitable visualization substrate. In the case of a fluorescent labelling, the visualization is made with the aid of a fluoro-Imager (Molecular Dynamics, Bondoufle, France) or any other apparatus capable of detecting the fluorescence emission. In the case of a labelling with digoxygenin (or with another antigen), the visualization is made with the aid of an anti-digoxygenin antibody (or an antibody specific for the antigen used for the labelling), coupled directly to an enzyme (alkaline phosphatase, peroxidase or any other enzyme), or in an indirect manner with an anti-digoxygenin antibody (or an antibody specific for the antigen used for the labelling) and an antibody coupled to an enzyme. A substrate suitable for the enzyme of the conjugate is used for the visualization. In the case of a labelling with ruthenium chelate (such as TBR), the visualization is performed by an electro-chemiluminescence reaction (G. F. Blackburn et al., Clin. Chem., 1991, 37:1534-1539).

A variant of this technique comprises the fixing of viral DNA on a microplate or another solid support and hybridization with a labelled probe as specified above.

Another variant of this technique comprises the fixing of an unlabelled probe on a microplate or another solid support and hybridization with the viral DNA of the sample which would have been labelled beforehand.

EXAMPLE 3

Diagnosis of an Erythrovirus Type V9 by Gene Amplification (PCR or Polymerase Chain Reaction) and Hybridization Viral DNA is extracted from a biological sample (blood, serum, plasma, amniotic fluid, bone marrow, tissue) with the aid of a QIAamp Blood Kit column conventional technique (Sambrook J. et al., 1989, *Molecular Cloning: A Laboratory Manual*. Cold Spring Harbor Laboratory Press, Cold Spring Harbor).

The probe is an oligonucleotide of 20-30 mers, a fragment of a sequence specific for V9 (SEQ ID NO:45 to 80, 108 and 110) or their complementary sequences. It is labelled in 3' with DIG-dUTP with the aid of the DIG Oligonucleotide Tailing kit (Boehringer Mannheim, Meylan, France).

The transfer membrane is prehybridized in a buffer comprising (50% formamide; 5×SSC; 2% of blocking reagent (Boehringer Mannheim, Meylan, France); 0.1% of N-laurylsarcosine; 0.02% of SDS), at 42° C. for 90 minutes. The hybridization is carried out in 3 ml of a buffer of the same composition with 10 µl of labelled probe at 42° C. for 16 hours. The membrane is washed twice in 2×SSC buffer containing 0.1% SDS at 60° C. for 10 minutes, and then twice in 1×SSC buffer containing 0.1% SDS at 60° C. for 10 minutes. The membrane is then visualized with DIG Luminescent Detection Kit (Boehringer Mannheim, Meylan, France) and an autoradiography.

EXAMPLE 4

Group Diagnosis and Differential Diagnosis of Type B19 and V9 Erythroviruses by Gene Amplification and Hybridization The viral DNA is extracted from a biological sample (blood, serum, plasma, amniotic fluid, bone marrow, tissue) with the aid of a QIAamp Blood Kit column (Qiagen S.A., France) or of any other method of extracting nucleic acids.

The PCR is carried out according to the method described by Saiki et al. (Nature, 1986, cited above) with 10 µl of DNA solution in a final volume of 100 µl of reaction mixture (50 mM KCl; 10 mM Tris-HCl pH 8.3; 2.5 mM MgCl$_2$; 200 µM dNTP; 25 pmol of sense and antisense oligonucleotides) with 1.5 IU of AmpliTaq Gold™ (Perkin Elmer, France). The amplification primers are oligonucleotides of 20 to 25 mers chosen so as to amplify the DNA of B19 and of the variant V9: the 2 (Qiagen S.A., France) or of any other method of extracting nucleic acids.

The PCR is carried out according to the method described by Saiki et al. (Nature, 1986, 324: 163-66) with 10 µl of DNA solution in a final volume of 100 µl of reaction mixture (50 mM KCl; 10 mM Tris-HCl pH 8.3; 2.5 mM MgCl$_2$; 200 µM dNTP; 25 pmol of sense and antisense oligonucleotides) with 1.5 IU of AmpliTaq Gold™ (Perkin Elmer, France). The amplification primers are oligonucleotides of 20 to 25 mers chosen so as to amplify only the DNA of the V9 variant: either the 2 primers (sense and antisense) are fragments of the sequences specific for V9 (SEQ ID NO:45 to 80, 108 and 110) or their complementary sequences, or one of the primers is chosen from the sequences specific for V9 (SEQ ID NO:45-80, 108 and 110) or their complementary sequences whereas the other primer is chosen from the sequences capable of hybridizing both the B19 erythro-viruses and the V9 erythroviruses (SEQ ID NO:2 to 44, 105-107, 109 and 111-112) or their complementary sequences. The temperature cycles are applied to the reaction mixture by a thermocycler (T9600, Perkin Elmer, France) according to the following programme:

1 Cycle:
6 minutes at 95° C.
5 Cycles:
60 seconds at 95° C.
30 seconds at 60° C.

30 seconds at 72° C.
45 Cycles:
30 seconds at 95° C.
30 seconds at 60° C.
30 seconds at 72° C.
1 Cycle:
5 minutes at 72° C.

The product of amplification is deposited on a 1.3% agarose gel so as to be subjected to an electro-phoretic separation and a transfer onto a nylon membrane loaded by capillarity according to a (sense and antisense) primers are fragments of the sequences capable of hybridizing both with the B19 erythroviruses and with the V9 erythroviruses (SEQ ID NO:2 to 44, 105-107, 109, 111-112) or of their complementary sequences. The temperature cycles are applied to the reaction mixture by a thermocycler (T9600, Perkin Elmer, France) according to the following programme:
1 Cycle:
6 minutes at 95° C.
5 Cycles:
60 seconds at 95° C.
seconds at 60° C.
seconds at 72° C.
45 Cycles:
30 seconds at 95° C.
seconds at 60° C.
seconds at 72° C.
1 cycle:
5 minutes at 72° C.

The product of amplification is deposited on a 1.3% agarose gel so as to be subjected to an electro-phoretic separation and a transfer onto a nylon membrane loaded by capillarity according to a conventional technique (Sambrook J. et al., 1989, cited above).

The probe is an oligonucleotide of 20-30 mers, a fragment of a sequence specific for V9 (SEQ ID NO:45 to 80, 108 and 110) or their complementary sequences, or alternatively specific for B19, or finally which hybridizes both with B19 and with V9 (SEQ ID NO:2 to 44 or 105-107, 109, 111-112), if it is sought to carry out a group diagnosis. It is labelled in 3' with DIG-dUTP with the aid of the DIG Oligonucleotide Tailing kit (Boehringer Mannheim, Meylan, France).

The transfer membrane is prehybridized and hybridized under the same conditions as those set out in Example 3.

EXAMPLE 5

Group Diagnosis and Differential Diagnosis of Type B19 and V9 Erythroviruses by Gene Amplification and Restriction Enzymes Extraction of the viral DNA from a biological sample (blood, serum, plasma, amniotic fluid, bone marrow, tissue) with the aid of a QIAamp Blood Kit column (Qiagen S.A., France) or of any other method of extracting nucleic acids.

The NS1a PCR is carried out according to the method described by Saiki et al. with 5 µl of DNA solution in a final volume of 50 µl of reaction mixture (50 mM KCl; 10 mM Tris-HCl pH 8.3; 2.5 mM MgCl$_2$; 200 µM dNTP; 12.5 pmol of sense and antisense oligonucleotides) with 1.5 IU of AmpliTaq Gold™ (Perkin Elmer, France) and the pair of primer B (sense primer e1905f, SEQ ID NO:105; and the antisense primer e1987r, SEQ ID NO:106) using the following temperature cycles (on a thermocycler T9700, Perkin Elmer, France):
1 Cycle:
6 minutes at 94° C.
5 Cycles:
30 seconds at 94° C.
1 minute at 55° C.
1 minute at 72° C.
45 Cycles:
30 seconds at 94° C.
30 seconds at 60° C.
30 seconds at 72° C.
1 Cycle:
7 minutes at 72° C.

An aliquot of the product of amplification (10 µl) was deposited on a 2% agarose gel so as to be subjected to an electrophoretic separation and a transfer onto a nylon membrane loaded by capillarity according to a conventional technique (J. Sambrook et al., 1989, cited above). The membrane was hybridized with an oligonucleotide probe of 36 mer, e1954fp (SEQ ID NO:121): ACCAGTATCAGCAGCAGTG-GTGGTGAAAGCTCTGAA, a fragment of the sequence SEQ ID NO:11. This probe allows a detection of type B19 and V9 erythroviruses.

An aliquot of the product of amplification (10 µl) was subjected to the action of the restriction enzyme MunI for 2 hours and then subjected to an electrophoretic separation on a 2% agarose gel. As described above, the erythrovirus type is B19 if there is cleavage, and V9 if there is no cleavage.

Results of the NS1a PCR:

79 samples found to be indeterminate or weakly positive with the old B19 PCR (Lefrere, et al., Transfusion, 1995, 35:389-391) were screened with the aid of the new NS1a PCR (consensus erythrovirus, sequences according to the invention). Of the 79 samples screened, 31 are positive and were typed with the aid of the restriction enzyme MunI: 18 (58%) were found to be of type B19 and 13 (42%) of type V9.

The samples which were positive by NS1a PCR were able to be amplified on 1100 bp by a nested PCR (S1S2 PCR) with the aid of the pair of primers e1855f (SEQ ID NO:113) and e2960r (SEQ ID NO:114) for the first amplification step of 30 cycles (PCRS1), and of the pair of primers e1863f (SEQ ID NO:115) and e2953r (SEQ ID NO:116) for the second amplification step of 50 cycles (PCRS2). 15 samples were found to be positive by S1S2 PCR and sequenced on 1110 bp (13 of type B19 by NS1A PCR and 2 of the variant type). The analysis of the sequences showed that:

the B primers (sense primer e1905f, SEQ ID NO:105; and antisense primer e1987r, SEQ ID NO:106), are perfectly conserved for all the 15 sequences (of the B19 and variant type) as well as for all the known B19 sequences, confirming their importance for use for a consensus diagnostic test for B19 and V9, the probe e1954fp (SEQ ID NO:121), a fragment of the sequence SEQ ID NO:11 is equally well conserved for the 15 sequences as well as for all the known B19 sequences, the B19 sequences form a well homogeneous group with less than 1.2% divergence between them (7 B19 sequences of GenBank and the 13 B19 sequences of this study), finally for the 2 sequences typed variant erythrovirus by NS1a PCR with MunI digestion, less than 4.5% divergence with V9 is observed.

EXAMPLE 6

Cloning of the Capsid Genes VP1 and VP2 of V9 into a Baculovirus Expression Vector First Step:
Cloning of the VP1 Gene into a Bacterial Plasmid
The VP1 gene of V9 is amplified by PCR according to the method described by Saiki et al. (Nature, 1986, 324:163-166)

with 10 µl of a 10⁻² dilution of V9 viral DNA in a final volume of 100 µl of reaction mixture (20 mM Tris-HCl pH 8.8; 10 mM KCl, 10 mm (NH$_4$)$_2$SO$_4$; 2 mM MgSC$_4$; 0.1% Triton X-100; 0.1 mg/ml of BSA; 0.2 mM dNTP; 25 pmol of sense primers (e2435fStuI/BglII: AAAGGCCTAGATCTTGTA-GATTATGAGTAAAAC, SEQ ID NO:117) and antisense primers (e4813rEcoRI: GGGAATTCGGTGGGTGACGGT-TCCTG, SEQ ID NO:118) with 2.5 U of Pfu Turbo™ (Stratagene, France). The amplification primers were chosen on the V9 sequence on either side of the VP1 gene, their 5' end was modified by addition of restriction site(s) (indicated in their name) in order to facilitate the cloning. The temperature cycles applied to the reaction mixture are the following:

1 Cycle:
1 minute at 94° C.
20 Cycles:
1 minute at 94° C.
1 minute at 55° C.
2.5 minutes at 72° C.
1 Cycle:
10 minutes at 72° C.

The product of amplification of the VP1 gene was purified with the aid of a silica column (QIAquick PCR Purification Kit, Qiagen, France) and then subjected to the action of the restriction enzymes StuI and EcoRI. After heat inactivation of the restriction enzymes (20 min at 65° C.), the VP1 gene fragment was purified by dialysis against H$_2$O on a 0.025 µm filter (VSWP01300, Millipore).

The plasmid pBacPAK8 (Clontech, France) is subjected to the action of the restriction enzymes StuI and EcoRI, the vector is then dephosphorylated with shrimp alkaline phosphatase (Boehringer, France). After heat inactivation of the restriction enzymes (20 min at 65° C.), the plasmid was purified with the QIAquick PCR Purification Kit (Qiagen).

The ligation is carried out with 50 ng of plasmid pBac-PAK8 and 100 ng of VP1 fragment (prepared as described above) with T4 ligase (Life Technologies, France). After heat inactivation of the T4 ligase (10 min at 65° C.), 2 μl of ligation product diluted ½ with water are electroporated with 25 μl of electro-competent bacteria (Epicurian Coli Sure Electroporation-Competent cells, Strategene). The electroporated bacteria are immediately taken up in 1 ml of SOC medium (2% tryptone, 0.5% of yeast extracts, 10 mM NaCl, 2.5 mM KCl, 10 mM $MgCl_2$, 10 mM $MgSO_4$ and 20 mM glucose), incubated for 1 h at 37° C., with stirring. Next, 10 μl, 100 μl and 890 μl of the transformed bacteria are plated on Lennox agar dishes (10 g/l of peptone, 5 g/l of yeast extracts, 5 g/l NaCl, and 13 g/l agar) containing 50 μg/ml of ampicillin. After 24 h of incubation at 37° C., 24 colonies per construct are subcultured in 5 ml of Lennox medium with 50 μg/ml of ampicillin and incubated for 24 h at 37° C., with stirring.

The plasmid DNA is extracted by alkaline minilysis with the aid of the QIAprep 8 Turbo miniprep kit (Qiagen) and analysed by StuI/EcoRI and KpnI/–HindIII restriction in order to determine the presence of the insert and its orientation. The clone pB8-VP1.C5 was selected and the recombinant plasmid was checked by sequencing cloning of the VP2 gene into a bacterial plasmid.

The VP2 gene of V9 is amplified by PCR according to the method described by Saiki et al. (Nature, 1986, 324:163-166) with 10 μl of a $10^{-2}$ dilution of V9 viral DNA in a final volume of 100 μl of reaction mixture (20 mM Tris-HCl pH 8.8; 10 mM KCl, 10 M $(NH_4)_2SO_4$; 2 mM $MgSO_4$; 0.1% Triton X-100; 0.1 mg/ml of BSA; 0.2 mM dNTP; 25 pmol of sense primers (e3115fBamHI: CACGGATCCATACCCCAGCATGACTTCAG, SEQ ID NO:119) and antisense primers (e4813rBamHI: CACGGATCCGGTGGGTGACGGTTCCTG, SEQ ID NO:120) with 2.5 U of Pfu Turbo™ (Stratagene, France). The amplification primers were chosen on the V9 sequence on either side of the VP2 gene, their 5' end was modified by addition of restriction site(s) (indicated in their name) in order to facilitate the cloning. The temperature cycles applied to the reaction mixture are the following:

1 Cycle:
1 minute at 94° C.
20 Cycles:
1 minute at 94° C.
1 minute at 60° C.
2.5 minutes at 72° C.
1 Cycle:
10 minutes at 72° C.

The product of amplification of the VP2 gene was purified with the aid of a silica column (QIAquick PCR Purification Kit, Qiagen, France) and then subjected to the action of the restriction enzymes BamHI. The VP2 gene fragment was purified by the QIAquick PCR Purification Kit (Qiagen).

The plasmid pBacPAK8 (Clontech, France) is subjected to the action of the restriction enzymes BamHI, the vector is then dephosphorylated with shrimp alkaline phosphatase (Boehringer, France). After heat inactivation of the shrimp alkaline phosphatase (20 min at 65° C.), the plasmid was purified by phenol/chloroform extraction and precipitated with ethanol.

The ligation is carried out with 50 ng of plasmid pBacPAK8 and 100 ng of VP2 fragment (prepared as described above) with T4 ligase (Life Technologies, France). After heat inactivation of the T4 ligase (10 min at 65° C.), 2 μl of ligation product diluted ½ with water are electroporated with 25 μl of electro-competent bacteria (Epicurian Coli Sure Electroporation-Competent cells, Stratagene). The electroporated bacteria are immediately taken up in 1 ml of SOC medium, incubated for 1 h at 37° C., with stirring. Next, 10 μl, 100 μl and 890 μl of the transformed bacteria are plated on Lennox agar dishes containing 50 μg/ml of ampicillin. After 24 h of incubation at 37° C., 24 colonies per construct are sub-cultured in 5 ml of Lennox medium with 50 μg/ml of ampicillin and incubated for 24 h at 37° C., with stirring.

The plasmid DNA is extracted by alkaline minilysis with the aid of the QIAprep 8 Turbo miniprep kit (Qiagen) and analysed by BamHI and SacI restriction in order to determine the presence of the insert and its orientation. The clone pB8-VP2.C20 was selected and the recombinant plasmid was checked by sequencing: a base A deleted just upstream of the initiator ATG of VP2 can be noted, but this mutation can be ignored: it will not generate the expression of VP2.

Second Step:

Construction of the Recombinant Baculovirus Expressing VP1

The plasmid pB8-VP1.C5 is cotransfected with the baculovirus BacPAk6, linearized with Bsu361 (BacPAK™ Baculovirus Expression System, Clontech), into SF9 insect cells with lipofectin. 2 isolations are performed by the lysis plaque method, the plaques isolated are transferred onto a nitrocellulose membrane, the membrane is then hybridized with a DNA probe specific for the VP1 gene of V9.

The recombinant baculovirus BacPAK6-pB8-VP1.C4.2 was thus selected. The expression of the VP1 protein was verified by Western Blotting on a cellular pellet of SF9 cells infected with this recombinant baculovirus. A band was observed at the expected size of VP1 (about 80 kDa) but which is not recognized by the anti-VP1-B19 monoclonal antibody (Argene, France). It is possible that this monoclonal antibody does not crossreact with the VP1 protein of V9.

The cloning into a baculovirus was verified by sequencing after PCR with the primers Bac1 and Bac2 (Clontech).

Construction of the Recombinant Baculovirus Expressing VP2

The plasmid pB8-VP2.C20 is cotransfected with the baculovirus BacPAk6, linearized with Bsu36I (BacPAK™ Baculovirus Expression System, Clontech), into SF9 insect cells with lipofectin. 2 isolations are performed by the lysis plaque method, the plaques isolated are transferred onto a nitrocellulose membrane, the membrane is then hybridized with a DNA probe specific for the VP2 gene of V9.

The recombinant baculovirus BacPAK6-pB8-VP2.-C1.3 is selected. The expression of the VP2 protein was verified by Western Blotting on a cellular pellet of SF9 cells infected with this recombinant baculovirus. The anti-VP2-B19 monoclonal antibody (Argene, France) indeed detects a protein with an apparent molecular weight of about 58 kDa which is also clearly visible on the acrylamide gel. Virus-like particles of about 20 to 30 nm in diameter are observed by electron microscopy in the culture supernatants of the SF9 cells after infection with a recombinant baculovirus expressing the VP2 protein of V9. The size and the appearance of the virus-like particles obtained are in every respect in conformity with those described for B19. This observation confirms that the VP2 protein of V9 is produced in a native form by the baculovirus, because it is capable of forming empty capsids by self-assembling.

The cloning into a baculovirus was verified by sequencing after PCR with the primers Bac1 and Bac2 (Clontech).

Third Step:

The proteins VP1 and VP2 of V9 expressed in a baculovirus will be purified so as to be used as a target antigen for new serological tests for the diagnosis of erythrovirus V9 infections.

As is evident from the above, the invention is not at all limited to its embodiments, implementations and applications which have just been described more explicitly; it encompasses on the contrary all the variants which may occur to the specialist in this field, without departing from the framework or the scope of the present invention.

The invention claimed is:

1. A method of making a polypeptide capable of being recognized by antibodies induced by an erythrovirus V9 or capable of inducing the production of antibodies to erythrovirus V9, the method comprising:

providing for expression of an erythrovirus V9 polypeptide in a host cell, said host cell transformed with a recombinant nucleic acid encoding a polypeptide comprising or consisting of an amino acid sequence selected from the group consisting of SEQ ID NO: 92, 101, 102, 103 or 104; and recovering the polypeptide.

2. The method of claim 1, wherein said recombinant nucleic acid encodes a polypeptide comprising SEQ ID NO: 92.

3. The method of claim 1, wherein said host cell is an insect cell.

4. The method of claim 3, wherein said insect cell is SF9.

5. The method of claim 1, wherein the polypeptide comprises the amino acid sequences of SEQ ID NO: 92.

6. The method of claim 5, wherein the polypeptide is recovered in the form of an empty viral capsid.

7. The method of claim 1, wherein said recombinant nucleic acid encodes a polypeptide comprising SEQ ID NO: 101.

8. The method of claim 1, wherein said recombinant nucleic acid encodes a polypeptide comprising SEQ ID NO: 102.

9. The method of claim 1, wherein said recombinant nucleic acid encodes a polypeptide comprising SEQ ID NO: 103.

10. The method of claim 1, wherein said recombinant nucleic acid encodes a polypeptide comprising SEQ ID NO: 104.

* * * * *